US009061076B2

(12) United States Patent
Franzen et al.

(10) Patent No.: US 9,061,076 B2
(45) Date of Patent: Jun. 23, 2015

(54) VIRAL NANOPARTICLE CELL-TARGETED DELIVERY PLATFORM

(75) Inventors: Stefan Franzen, Apex, NC (US); Richard Guenther, Cary, NC (US); Steven A. Lommel, Cary, NC (US); LiNa Loo, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 1579 days.

(21) Appl. No.: 12/601,736

(22) PCT Filed: May 22, 2008

(86) PCT No.: PCT/US2008/006540
§ 371 (c)(1), (2), (4) Date: Oct. 27, 2011

(87) PCT Pub. No.: WO2008/153725
PCT Pub. Date: Dec. 18, 2008

(65) Prior Publication Data
US 2012/0039799 A1 Feb. 16, 2012

Related U.S. Application Data

(60) Provisional application No. 60/940,277, filed on May 25, 2007.

(51) Int. Cl.

| | |
|---|---|
| ***A61K 31/704*** | (2006.01) |
| ***A61P 35/00*** | (2006.01) |
| ***A61K 51/00*** | (2006.01) |
| ***C12N 15/09*** | (2006.01) |
| ***A61K 47/48*** | (2006.01) |
| ***A61K 9/51*** | (2006.01) |
| ***B82Y 5/00*** | (2011.01) |
| ***C12N 7/00*** | (2006.01) |

(52) U.S. Cl.
CPC ......... *A61K 47/48776* (2013.01); *A61K 9/5184* (2013.01); *A61K 47/48276* (2013.01); *A61K 47/48315* (2013.01); *B82Y 5/00* (2013.01); *C12N 7/00* (2013.01); *C12N 15/09* (2013.01); *C12N 2770/38023* (2013.01); *C12N 2770/38043* (2013.01); *C12N 2799/02* (2013.01); *C12N 2810/855* (2013.01)

(58) Field of Classification Search
None
See application file for complete search history.

(56) References Cited

U.S. PATENT DOCUMENTS

| | | | | |
|---|---|---|---|---|
| 6,703,237 | B2 | 3/2004 | Samulski et al. | |
| 7,285,275 | B2 | 10/2007 | Matsuzawa et al. | |
| 7,396,811 | B2 | 7/2008 | LeBowitz et al. | |
| 7,425,323 | B2 | 9/2008 | Schiltz et al. | |
| 7,560,424 | B2 | 7/2009 | LeBowitz et al. | |
| 7,629,309 | B2 | 12/2009 | LeBowitz et al. | |
| 7,824,660 | B2 | 11/2010 | Buzatu et al. | |
| 7,858,576 | B2 | 12/2010 | LeBowitz et al. | |
| 8,455,644 | B2 | 6/2013 | Bazhina et al. | |
| 8,518,419 | B2 | 8/2013 | Gunton et al. | |
| 8,518,643 | B2 | 8/2013 | Rank et al. | |
| 8,518,981 | B2 | 8/2013 | Calderari et al. | |
| 8,524,276 | B2 | 9/2013 | Shah et al. | |
| 8,535,718 | B2 | 9/2013 | Dansereau et al. | |
| 8,541,550 | B2 | 9/2013 | Khan et al. | |
| 8,562,962 | B2 | 10/2013 | Schiltz et al. | |
| 8,603,988 | B2 | 12/2013 | Reynolds et al. | |
| 8,765,787 | B2 | 7/2014 | Aberg et al. | |
| 2004/0018557 | A1 * | 1/2004 | Qu et al. | 435/7.1 |
| 2005/0234222 | A1 | 10/2005 | Deonarain et al. | |
| 2006/0216238 | A1 | 9/2006 | Manchester et al. | |
| 2007/0157328 | A1 | 7/2007 | Ramrakha et al. | |
| 2007/0258889 | A1 | 11/2007 | Douglas et al. | |
| 2012/0039799 | A1 * | 2/2012 | Franzen et al. | 424/1.17 |

OTHER PUBLICATIONS

Klonisch et al. (Trends in Molecular Medicine. 2008; 14 (10): 450-460).*
Ren et al. (Bioconjugate Chemistry. 2007; 18: 836-843).*
Huang et al. (Journal of Virology. 2000; 74 (7): 3149-3155).*
Ren et al. (Journal of General Virology. 2006; 87: 2749-2754).*
Joelson et al. (Journal of General Virology. 1997; 78: 1213-1217).*
Khor et al (Journal of General Virology. 2002; 76 (9): 4412-4419).*
Tkachenko et al. (Bioconjugate Chemistry. 2004; 15: 482-490).*
Anderson et al. (Cancer Research. 2004;; 64: 4919-4926).*
Gewirtz (Biochemical Pharmacology. 1999; 57: 727-741).*
Douglas et al. (Nature. 1998; 393: 152-155).*
You et al. (Journal of General Virology. 1995; 76 (11): 2841-2845).*
International Search Report and Written Opinion, PCT/US2008/006540, mailed Mar. 4, 2009.
Speir JA et al. Structures of the native and swollen forms of cowpea chlorotic mottle virus determined by X-ray crystallography and cryo-electron microscopy. Structure. 1995; 3(1): 63-78.
Loo L et al. Controlled encapsidation of gold nanoparticles by a viral protein shell. J. Am. Chem. Soc. Apr. 12, 2006; 128(14): 4502-4503.
Sherman MB et al. Removal of divalent cations induces structural transitions in *Red clover necrotic mosaic virus*, revealing a potential mechanism for RNA release. Journal of Virology. Nov. 2006; 80(21): 10395-10406.

(Continued)

*Primary Examiner* — Shanon A Foley
(74) *Attorney, Agent, or Firm* — Myers Bigel Sibley & Sajovec

(57) ABSTRACT

This invention is a process for the manufacture of a plant viral capsid to be used for the targeted delivery of therapeutics to diseased cells. The process uses a plant virus as the starting material. The choice of the plant virus overcomes a problem in the manufacture of a uniform starting material. The final product has an advantage over other plant virus-based delivery systems in that the plant virus selected has a natural structure that is resistant to breakdown during the delivery process. This system takes advantage of the reversible divalent cation switch that this capsid employs to assemble and disassemble.

28 Claims, 11 Drawing Sheets

(56) References Cited

OTHER PUBLICATIONS

Overton KW et al. Cellular uptake of modified *Red clover necrotic mosaic virus* and small molecule release from the virion. AICHE Annual Meeting, Conference Proceedings—2007 AICHE Annual Meeting, 2007 American Institute of Chemical Engineers US. 2007, 11 pp.

Loo L et al. Infusion of dye molecules into *Red clover necrotic mosaic virus*. Chemical Communications. Jan. 7, 2008; 1: 88-90.

Young M et al. Plant viruses as biotemplates for materials and their use in nanotechnology. Annu. Rev. Phytopathol. 2008; 46: 361-84.

Capsid, definition found in Webster's New Collegiate Dictionary p. 165 (1974).

Isea et al. "Can the RNA of the cowpea chlorotic mottle virus be released through a channel by means of free diffusion? A test in silico", *Biophys. Chem.* 107:101-106 (2004).

* cited by examiner

SEQUENCE LISTING

```
<160> NUMBER OF SEQ ID NOS: 9

<210> SEQ ID NO 1
<211> LENGTH: 34
<212> TYPE: RNA
```

-continued

<213> ORGANISM: Artificial
<220> FEATURE:
<223> OTHER INFORMATION: RNA virus trans-activating RNA sequence

<400> SEQUENCE: 1
ucaaucagag guaucgcccc gccucucagu guug 34

<210> SEQ ID NO 2
<211> LENGTH: 21
<212> TYPE: RNA
<213> ORGANISM: Artificial
<220> FEATURE:
<223> OTHER INFORMATION: RNA virus trans-activating RNA sequence

<400> SEQUENCE: 2
agagguaucg ccccgccucu c 21

<210> SEQ ID NO 3
<211> LENGTH: 13
<212> TYPE: PRT
<213> ORGANISM: Artificial
<220> FEATURE:
<223> OTHER INFORMATION: CD46 targeting peptide sequence

<400> SEQUENCE: 3

Cys Gly Gly Phe Ser Thr Ser Lys Arg Ala Arg Lys Ala
1 5 10

<210> SEQ ID NO 4
<211> LENGTH: 14
<212> TYPE: PRT
<213> ORGANISM: Artificial
<220> FEATURE:
<223> OTHER INFORMATION: HER2 targeting peptide sequence

<400> SEQUENCE: 4

Phe Cys Gly Asp Gly Phe Tyr Ala Cys Tyr Met Asp Val Lys
1 5 10

<210> SEQ ID NO 5
<211> LENGTH: 14
<212> TYPE: PRT
<213> ORGANISM: Artificial
<220> FEATURE:
<223> OTHER INFORMATION: CXCR4 targeting peptide sequence
<220> FEATURE:
<221> NAME/KEY: MISC_FEATURE
<222> LOCATION: (3)..(3)
<223> OTHER INFORMATION: Xaa is L-3(2-naphthyl)alanine
<220> FEATURE:
<221> NAME/KEY: MISC_FEATURE
<222> LOCATION: (8)..(8)
<223> OTHER INFORMATION: Xaa is D-lysine
<220> FEATURE:
<221> NAME/KEY: MISC_FEATURE
<222> LOCATION: (12)..(12)
<223> OTHER INFORMATION: Xaa is L-citrulline

<400> SEQUENCE: 5

Arg Arg Xaa Cys Tyr Arg Lys Xaa Pro Tyr Arg Xaa Cys Arg
1 5 10

<210> SEQ ID NO 6
<211> LENGTH: 13
<212> TYPE: PRT
<213> ORGANISM: Artificial
<220> FEATURE:
<223> OTHER INFORMATION: SV40 NLS targeting peptide sequence -continued

```
<400> SEQUENCE: 6

Cys Gly Gly Gly Pro Lys Lys Lys Arg Lys Val Gly Gly
1               5                   10


<210> SEQ ID NO 7
<211> LENGTH: 14
<212> TYPE: PRT
<213> ORGANISM: Artificial
<220> FEATURE:
<223> OTHER INFORMATION: HIV-1 Tat protein NLS targeting peptide
      sequence

<400> SEQUENCE: 7

Cys Gly Gly Arg Lys Lys Arg Arg Gln Arg Arg Arg Ala Pro
1               5                   10


<210> SEQ ID NO 8
<211> LENGTH: 13
<212> TYPE: PRT
<213> ORGANISM: Artificial
<220> FEATURE:
<223> OTHER INFORMATION: Adenovirus NLS targeting peptide sequence

<400> SEQUENCE: 8

Cys Gly Gly Phe Ser Thr Ser Leu Arg Ala Arg Lys Ala
1               5                   10


<210> SEQ ID NO 9
<211> LENGTH: 15
<212> TYPE: PRT
<213> ORGANISM: Artificial
<220> FEATURE:
<223> OTHER INFORMATION: IBD-oligolysine targeting peptide sequence

<400> SEQUENCE: 9

Cys Lys Lys Lys Lys Lys Lys Gly Gly Arg Gly Asp Met Phe Gly
1               5                   10                  15
```

VIRAL NANOPARTICLE CELL-TARGETED DELIVERY PLATFORM

RELATED APPLICATIONS

This application is a 35 U.S.C. §371 national phase application of PCT Application PCT/US2008/006540, filed May 22, 2008, and published in English on Dec. 18, 2008, as International Publication No. WO 2008/153725, and which claims the benefit under 35 U.S.C. §119(e) of U.S. Provisional Patent Application Ser. No. 60/940,277, filed May 25, 2007, the disclosure of each of which is incorporated herein by reference in its entirety.

GOVERNMENT SUPPORT

This invention was made with Government support under National Institutes of Health grant NCI CA098194. The United States Government has certain rights to this invention.

FIELD OF THE INVENTION

The present invention provides methods and compositions directed to the cellular and nuclear targeting of compounds of interests to cells of interest in mammals thereof in need.

BACKGROUND OF THE INVENTION

There are two main problems in conventional chemotherapy. 1) Metastasis may result generating numerous new neoplasms that require repeated treatment and 2) multi-drug resistance may develop in cancer cells, rendering the drugs useless since they are effectively pumped out. Based on the over expression of certain cell-surface receptors in cancer cells relative to normal cells, targeted cancer therapy aims to address the first problem by delivering cytotoxic agents specifically to primary tumors and metastatic cells. However, there are few, if any, targeted delivery strategies that can overcome multi-drug resistance (MDR). MDR arises because of the over expression of trans-membrane pumps known as efflux transporters. Efflux transporters belong to the ATP-binding cassette (ABC) family of membrane proteins, which includes Pglycoprotein. When they are over expressed on a cancer cell, it gains capacity to pump a wide range of anti-cancer drugs out of the cytoplasm, hence the name multi-drug resistance. Many current chemotherapy drugs work by damaging DNA, and thus inhibiting replication of rapidly dividing cancer cells. Consequently, these drugs must concentrate in the nucleus for optimal function. For example, the drug DOX targets the site of topoisomerase II action.

Previously used delivery platforms include metallic nanoparticles, liposomes, viruses and polymeric drug delivery systems. Numerous virus vectors have been studied for cancer treatment, some with promising clinical results. However, the FDA has not approved any virus-based therapeutic agent due to concerns about toxicity that became apparent in the 1999 Gelsinger gene therapy accident. This incident raised concerns regarding the immune response to human adenoviral vectors. In addition to immunogenicity, Adenovirus must be genetically disabled for use as a drug or gene delivery platform. From a regulatory perspective, even the low probability event of Adenovirus recombination is sufficient to impede its development and use as a vector.

Plant viruses provide an alternative strategy for drug, and potentially gene, delivery. Preliminary research indicates that non-enveloped icosahedral viruses also have potential for targeted cell delivery as multifunctional nanoparticles. One of the best-characterized viruses for nanotechnology applications is Cowpea chlorotic mottle virus (CCMV) (X. X. Zhao, et al., *Virology,* 207:486-494 (1995); A. Zlotnick, et al., *Virology,* 277:450-456 (2000); L. O. Liepold, et al., *Physical Biology,* 2:S166-S172 (2005); F. D. Sikkema, et al., *Organic & Biomolecular Chemistry,* 5:54-57 (2007), which has the ability to assemble in vitro. Also, Cowpea mosaic virus (CPMV) has been investigated for use as a delivery agent (M. Manchester and P. Singh, *Advanced Drug Delivery Reviews,* 58:1505-1522 (2006); G. Basu, et al., *Journal of Biological Inorganic Chemistry,* 8:721-725 (2003); S. Sen Gupta, et al., *Bioconjugate Chemistry,* 16:1572-1579 (2005); P. Singh, et al., *Drug Development Research,* 67:23-41, (2006)). Expression of a peptide on the C-terminus (T. Joelson, et al, *Journal of General Virology,* 78:1213-1217 (1997)) and coat polymorphism studies (C. Hsu, et al., *Virology,* 349:222-229 (2006)) of Tomato bushy stunt virus (TBSV) demonstrates a genetic approach to preparation of targeting PVNs (E. Gillitzer, et al., *Chemical Communications,* 2390-2391 (2002)). These viruses have been proposed as a delivery platform based on their ease of modification, low toxicity, and lack of replication in humans.

SUMMARY OF THE INVENTION

The present invention overcomes previous shortcomings in the art by employing a plant virus with a divalent cation switch-responsive capsid, which takes advantage of the different physiological conditions intra and extracellularly, to permit delivery of compounds of interest loaded inside such capsids into the nucleus of cells of interest without risk of infection by the capsids.

A first aspect of the present invention provides a method of enclosing a compound of interest in plant viral capsids, comprising the steps of treating viral capsids to remove divalent cations to open pores therein, thereby providing sensitized viral capsids; incubating the sensitized viral capsids with the compound of interest for a time sufficient for the compound of interest to enter the sensitized viral capsids; and treating the viral capsids with divalent cations for a time sufficient to close the pores and enclose the compound of interest in the plant viral capsids.

A further aspect of the present invention is a plant viral capsid having a compound of interest enclosed therein. The plant viral capsid having a nuclear targeting compound coupled thereto, the plant viral capsid can be produced by (z) treating viral capsids with a chelating agent to open pores therein, thereby providing sensitized viral capsids; (ii) incubating the sensitized viral capsids with the compound of interest for a time sufficient for the compound of interest to enter the sensitized viral capsids; (iii) treating the viral capsids with divalent cations for a time sufficient to close the pores and enclose the compound of interest in the plant viral capsids.

Another aspect of the present invention is a method of delivering a compound of interest to the nucleus of cells of interest, which cells are in vitro or in a subject such as a mammalian subject in need thereof, comprising providing plant viral capsids having the compound of interest enclosed therein, the plant viral capsids further comprising: (i) a cell targeting compound coupled thereto and (ii) a nuclear targeting compound coupled thereto; and then administering the plant viral capsids to the cells of interest or the subject in an amount effective for said compound of interest to be delivered to the nucleus (or other sub-cellular organelle) of said cells of interest (that is, not released in the cytoplasm, but released in the nucleus or other subcellular organelle of interest). While the nucleus is a target of considerable interest for purposes such as delivering chemotherapeutic drugs, the invention can also be used to target other organelles, and hence can be considered a general two-stage targeting delivery vehicle. This feature is analogous to infectious viruses, but in the present invention the capability derives from the addition of targeting peptides or other targeting molecules added to the capsid of the non-infectious plant virus.

The present invention is explained in greater detail in the drawings herein and the specification set forth below. The disclosures of all patent references cited herein are to be incorporated by reference herein in their entirety.

DETAILED DESCRIPTION OF THE INVENTION

Figure 1:
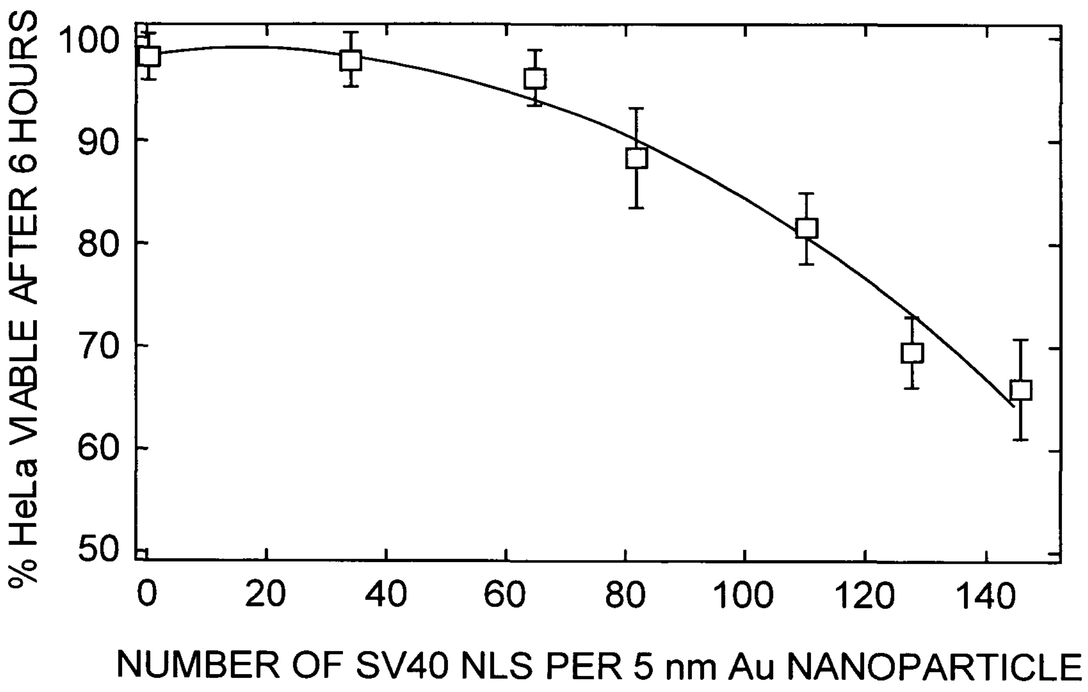
FIG. 1. Cytotoxicity data as a function of coverage of an Au nanoparticle by the NLS from SV40.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to specify exhaustively all permutations, combinations and variations thereof.

A. DEFINITIONS

As used in the description of the invention and the appended claims, the singular forms “a”, “an” and “the” are intended to include the plural forms as well, unless the context clearly indicates otherwise. Furthermore, the term “about,” as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, “and/or” refers to and encompasses any and all possible combinations of one or more of the associated listed items, as well as the lack of combinations when interpreted in the alternative (“or”).

The disclosures of all Patent references cited herein are incorporated herein by reference in their entirety.

“Virus” as used herein refers to an acellular organism whose genome consists of nucleic acid, and which obligately replicates inside host cells using host metabolic machinery and ribosomes to form a pool of components that assemble into particles called virions, which serve to protect the genome and to transfer it to other cells. As used herein a “plant virus” is a virus that infects plants. In a preferred embodiment, the plant virus is Red clover necrotic mosaic virus (RCNMV). In another embodiment, the plant virus is a Dianthovirus. In another embodiment, the plant virus is a Tombusviridae plant virus. The virus is in some embodiments an icosahedral virus (e.g., T1, T3, T5, T7, T9, T13, T25 viruses, etc.). See, e.g., U.S. Pat. Nos. 7,371,755; 7,132,105; 5,804,439; and 5,602,242. The virus is in some embodiments a virus that infects plants, fungi and algae.

“Virion” as used herein refers to virus particles. A virion is an inert carrier of viral genomic DNA or RNA that is assembled inside cells from virus-specified components and that is a complete infective particle.

“Capsid” as used herein refers to the protein shell that encloses viral genomic DNA or RNA in its central cavity comprising several monomeric capsid protein subunits. Further, a viral capsid can contain other modifications, including insertions, deletions and/or substitutions. As used herein a “plant virus capsid” refers to a capsid structure of a plant virus, including a viral genomic ex segment facilitating capsid protein assembly of the same or another virus according to prior developed techniques (R. H. Guenther, et al., *Nucleic Acids Research,* 32:2819-2828 (2004)). In a preferred embodiment RCNMV plant virus capsids are used. In another embodiment, Dianthovirus plant virus capsids are used. In another embodiment, Tombusviridae plant virus capsids are used.

“Origin of assembly” or “origin of initiation” as used herein refers to nucleic acid duplex, such as an RNA duplex, that is necessary for the assembly of individual viral coat protein subunits into the plant viral capsid. These have sometimes also been called transactivating nucleic acid segments. See, e.g., Lommel and Sit, U.S. Pat. No. 6,433,248 (The disclosure of which is incorporated by reference herein in its entirety.). Specific examples include, but are not limited to; (a) an RNA consisting of the sequence: UCAAUCAGAGGUAUCGCCCCGCCUCUCAGUGUUG (SEQ ID NO: 1)

and (b) an RNA consisting of the sequence: AGAGGUAUCGCCCCGCCUCUC (SEQ ID NO:2).

"Polyanion" as used herein may be any suitable polyanion, preferably included in an amount sufficient to support self-assembly of the viral capsid following initiation of assembly by the origin of assembly as noted above. Examples of suitable polyanions include, but are not limited to, succinylated PLL, succinylated PEI, polyglutamic acid, polyaspartic acid, polyacrylic acid, polymethacrylic acid, dextran sulfate, heparin, hyaluronic acid, DNA, RNA, and negatively charged proteins (see, e.g., U.S. Pat. No. 6,881,576); heparan sulfate, dermatan sulfate, chondroitin sulfate, pentosan sulfate, keratan sulfate, mucopolysaccharide polysulfate, carrageenan, sodium alginate, potassium alginate, hyaluronic acid, and carboxymethylcellulose (see, e.g., US Patent Application No. 2007/0110813); sucrose octasulfate, or inositol hexaphosphate (see, e.g., Patent Application No. 2007/0116753). In some embodiments, polyanion refers to the native bipartite RNA genome (RNA-1 and RNA-2) or any combination of said genome including non-native sequences or polymeric materials of negative charge.

Plant viral capsid proteins may be modified such as to provide novel characteristics beneficial for use under the invention. For example, one or more amino acids comprising the inner wall of a virion cavity may be modified (e.g., by site-directed mutagenesis) to provide for novel chemical environments in the cavity. Thus, positive charge in the cavity may be increased through modifications adding, for example, additional lysine and/or arginine residues. Similarly, the negative charge of the cavity may be increased through, for example, the addition of the specifically placed glutamic and/or aspartic acid residues. In a like manner, the hydrophobicity of the cavity may be selectively altered through use of an appropriate substituted amino acid.

Chemical modifications and functionalization may also be used to modify plant viral capsid cavities. For example, the cavity may be modified by addition of thiols with the potential to form disulfides or react with metals (e.g., cadmium, gold).

Additionally, amino acids in exposed capsid proteins on the outer surface of a viral capsid may be modified to create novel properties. See, e.g., U.S. Pat. No. 5,248,589. For example, such amino acid residues may be covalently linked to targeting compounds to provide for directed targeting of the plant viral capsid to particular tissues in therapeutic and imaging techniques. As another example, the outer surface may be modified and/or functionalized with reactive groups that enhance interactions with surfaces. Covalent modifications to increase the stability of the virion, or provide a site for further chemical modification, may also be used. Additional cysteine substitutions are particularly preferred in this embodiment.

In some embodiments, the targeting compound is included onto said plant viral capsid surface by modification of the plant viral genome to produce a coat protein with altered sequence.

"Cell of interest" as used herein may be any suitable cell, including but not limited to cancer cells, tissue cells generally (e.g., muscle, bone, nerve, liver, lung, etc.), pathological and non-pathological microbial cells (e.g., bacterial, mycobacterial, spirochetal rickettsial, chlamydial, mycoplasmal, and fungal, etc.), parasitic cells (e.g., protozoal, helminth, etc.), and plant cells, etc.

"Cancer cell" as used herein may be any cancer cell, including, but not limited to, lung, colon, breast, ovarian, prostate, bone, nerve, liver, leukemia, and lymphoma cells. In some embodiments the cancer cell is a multidrug resistant cancer cell (see, e.g., U.S. Pat. Nos. 7,304,053; 7,091,226; 7,067,551) or a cancer stem cell, as the constructs described herein tend to evade the MDR transporters.

"Subjects" as used herein are, in general, mammalian subjects, including but not limited to human subjects and animal subjects (e.g., dogs, cats, cows, horses, rabbits, sheep, etc.) for veterinary purposes. Subjects may be afflicted with cancer, including but not limited to lung, colon, breast, ovarian, prostate, bone, nerve, and liver cancer, leukemia and lymphoma. In some embodiments the patient is afflicted with a multidrug resistant cancer, as the constructs described herein tend to evade the MDR transporters.

B. COMPOUND OF INTEREST

"Compound of interest" as used herein includes, but is not limited to, detectable compounds (including labelled compounds and detectable compounds in elemental form) and active compounds.

In some embodiments, the compound of interest is a positively charged or electrically neutral compound. Without wishing to be bound to any particular theory, it is believed that electrostatic attraction drives the uptake of a positively charged or electrically neutral compound into the pores in the plant viral capsid. In some embodiments, the compounds may have a Stokes radius of up to 15, 18, or 20 Angstroms.

In some embodiments, the compound of interest is a fluorescent compound or a chemiluminescent compound. In some embodiments, the compound of interest is a fluorescent compound, whereby fluorescence of such a compound is quenched when the fluorescent compound loaded into a plant viral capsid and fluorescence is not quenched when the fluorescent compound is released from inside a plant viral capsid, and whereby release of the fluorescent compound can be monitored by the measurement of increase in fluorescence quantum yield.

"Detectable compounds" as used herein include, but are not limited to, radiolabels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein), a fluorescent protein including, but not limited to, green fluorescent protein or one of its many modified forms, a nucleic acid segment in accordance with known techniques, and energy absorbing and energy emitting agents.

"Active compound" as used herein includes, but is not limited to, cytotoxic nucleosides or nucleotides, antisense oligonucleotides, radionuclides, energy absorbing and energy emitting agents, and other cytotoxic agents. Other cytotoxic (or "antineoplastic") agents include, but are not limited to, ricin (or more particularly the ricin A chain), aclacinomycin, diphtheria toxin, Monensin, Verrucarin A, Abrin, Tricothecenes, and *Pseudomonas* exotoxin A, taxol, cytochalasin B, gramicidin D, ethidium bromide, emetine, mitomycin, etoposide, tenoposide, anti-mitotic agents such as the vinca alkaloids (e.g., vincristine and vinblastine), colchicin, anthracyclines (e.g., doxorubicin, daunorubicin, epirubicin and idarubicin and analogs thereof), dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thiotepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including but not limited to, dactinomycin (formerly actinomycin), bleomycin, mithramycin, calicheamicin, and anthramycin (AMC).

Additional examples of antineoplastic or cytotoxic compounds that may be used as active compounds herein include but are not limited to: cisplatin, doxorubicin, taxotere, taxol, etoposide, irinotecan, camptostar, topotecan, paclitaxel, docetaxel, epothilones, tamoxifen, 5-fluorouracil, methoxtrexate, 5FU, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17. alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, CPT-11, Anastrazole, Letrazole, Capecitabine, Reloxafine, Droloxafine, or Hexamethylmelamine (See, e.g., U.S. Pat. No. 7,354,921 to Schering); a mechlorethamine, chlorambucil, cyclophosphamide, melphalan, ifosfamide, methotrexate, 6-mercaptopurine, 5-fluorouracil, cytarabile, gemcitabine, vinblastine, vincristine, vinorelbine, paclitaxel, etoposide, irinotecan, topotecan, doxorubicin, bleomycin, mitomycin, carmustine, lomustine, cisplatin, carboplatin, tamoxifen, leuprolide, flutamide, and megestrol, imatinib, adriamycin, dexamethasone, or cyclophosphamide (See, e.g., U.S. Pat. No. 7,358,258 to Genentech).

Active compounds may be oligonucleotides, e.g., DNA, RNA, cDNA, PNA, genomic DNA, and synthetic oligonucleotides, such as antisense oligonucleotides, etc. Such oligonucleotides are typically from 10, 12 or 15 nucleotide bases in length up to 30, 50 or 100 nucleotide bases in length, or more. Active compounds may be noncoding regulatory RNAs.

"Noncoding regulatory RNAs" (ncRNA) as used herein includes both natural and synthetic ncRNAs. Examples include, but are not limited to, small interfering RNA (siRNA), micro RNA (miRNA), piRNAs, ribosomal RNA (rRNA), small nuclear RNA (snRNA), small non-mRNA (snmRNA), small nucleolar RNA (snoRNA), small temporal RNA (stRNA) and other RNAs that regulate the function of mRNAs. See, e.g., D. Bartel et al., PCT Application Publication No. WO 2005/102298; see also T. Kowalik et al., US Patent Application Publication No. 20050186589. Some ncRNAs may be in the form of a natural or synthetic short hairpin RNA or "shRNA," which short hairpin RNA may or may not be subsequently processed to form a mature ncRNA. In general, ncRNAs as used herein may be any suitable length, but are typically short, e.g., from 5, 10 or 15 nucleotides in length, up to 25, 30 or 35 nucleotides in length. Nucleic acids encoding ncRNAs as used herein may be natural or synthetic and may be derived from any suitable source, including plant, animal, and microbe sources as described herein.

"Small interfering RNA" or "siRNA" (sometimes also referred to as short interfering RNA or silencing RNA) as used herein has its ordinary meaning in the art. In general, siRNAs are double-stranded RNA molecules that are 15 or 20 nucleotides in length, up to 25 or 30 nucleotides in length. siRNAs are known. See, e.g., U.S. Pat. Nos. 7,101,995; 6,977,152; and 6,974,680.

"MicroRNA" or "miRNA" as used herein has its ordinary meaning in the art. Typically, a miRNA is an RNA molecule derived from genomic loci processed from transcripts that can form local RNA precursor miRNA structures. The mature miRNA usually has 20, 21, 22, 23, or 24 nucleotides, although in some cases it may include a greater of lesser number of nucleotides, for example, between 18 and 26 nucleotides. The miRNA has the potential to pair with flanking genomic sequences, placing the mature miRNA within an imperfect RNA duplex which may be needed for its processing from a longer precursor transcript. In animals, this processing may occur through the action of Drosha and Dicer endonucleases, which excise a miRNA duplex from the hairpin portion of the longer primary transcript. The miRNA duplex comprises the miRNA and a similar-sized segment known as the miRNA* (miRNA star) from the other arm of the stem-loop. See, e.g., US Patent Application Publication No. 20060185027.

"Radionuclide" as used herein may be any radionuclide suitable for delivering a therapeutic dosage of radiation to a target cell such as a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117}$mSn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

Chemically linking fluorescent or chemiluminescent labels to nucleotides is well-known in the art (e.g., U.S. Pat. Nos. 4,811,218 and 4,855,225). Exemplary chemiluminescent labels are 1,2-dioxetane compounds (U.S. Pat. No. 4,931,223; Bronstein, et al. (1994) *Anal. Biochemistry* 219: 169-81). Fluorescent dyes useful for labeling nucleotide 5'-triphosphates include fluoresceins (Menchen, et al. (1993) U.S. Pat. No. 5,188,934), rhodamines (U.S. Pat. No. 5,366,860), cyanines (WO 97/45539), and metal porphyrin complexes (WO 88/04777).

Fluorescein dyes are well-known in the art and include, but are not limited to, fluorescein isothiocyanate, 6-carboxyfluorescein (6-FAM); 2',4',1,4,-tetrachlorofluorescein (TET); 2',4',5',7',1,4-hexachlorofluorescein (HEX); 2',7'-dimethoxy-4',5'-dichloro-6-carboxyrhodamine (JOE); 2'-chloro-5'-fluoro-7',8'-fused phenyl-1,4-dichloro-6-carboxyfluoresccin (NED); and T-chloro-T-phenyl-1,4-dichloro-6-carboxyfluorescein (VIC), CY3™, CY5™, CY3.5™, CY5.5™ and the like.

C. METHODS OF MAKING

As noted above, the present invention describes a method of enclosing a compound of interest in plant viral capsids. In general, the method comprises the steps of (a) treating viral capsids (e.g., with a chelating agent or by dialysis) to remove sufficient divalent cations (e.g., sufficient $Ca^{2+}$, sufficient $Mg^{2+}$, or most preferably remove sufficient of both $Ca^{2+}$ and $Mg^{2+}$) and open pores therein, thereby providing sensitized viral capsids; (b) incubating the sensitized viral capsids with the compound of interest for a time sufficient for said compound of interest to enter said sensitized viral capsids; and (c) treating said viral capsids with divalent cations for a time sufficient to close said pores and enclose said compound of interest in said plant viral capsids. The foregoing steps are typically carried out in an aqueous media or solution.

Plant viral capsids for use in the method can be produced in vivo in plant tissue or assembled in vitro (e.g., in a cell free system). Typically, in either system, an anionic origin of assembly (comprising a segment of RNA, typically about 40 or 50 nucleotides or more in length) is included to initiate the assembly of viral the viral capsid from the (one or more) viral proteins (e.g., natural coat proteins; recombinant or fusion proteins comprised of natural coat proteins and a targeting protein or peptide, combinations thereof). The origin of assembly can be the entire native viral RNA that contains the origin of assembly or a fragment thereof that contains the origin of assembly (typically at least 40 to 50 nucleotides in length). In addition, and in either system, there is typically included a polyanion sufficient to continue or propagate assembly of intact viral capsids following initiation of assembly. Without wishing to be bound to any particular theory, it is thought that plant viral capsids are stabilized by the presence of the origin of assembly and polyanion inside of the capsid shell. Any suitable polyanion may be used, with RNA being one example. When RNA is used as the polyanion any suitable RNA may be used, preferably from 1 or 1.5 kilobases to 5.5 or 6 kilobases in length, or more. Suitable RNAs include but are not limited to native viral RNA (preferably containing at least one or two mutations to render the RNA inactive) and synthetic RNA.

As noted above in connection with U.S. Pat. No. 6,433,248 to Lommel & Sit, RNA virus trans-activating RNA (or a synthetic oligonucleotide thereof) can be used as the origin of assembly. Examples of such nucleic acids include but are not limited to: (a) an RNA containing the sequence:

(SEQ ID NO: 1)
UCAAUCAGAGGUAUCGCCCCGCCUCUCAGUGUUG and (b) an RNA containing the sequence:
AGAGGUAUCGCCCCGCCUCUC (SEQ ID NO:2). The nucleic acid is preferably at least 15, 18 or 20 nucleotides in length, and in one embodiment is preferably not more than 40, 50 or 60 nucleotides in length. In another embodiment, the nucleotide may be incorporated into a longer molecule up to 400, 500, or 600 nucleotides in length or more. Fragments of (a) to (c) above which retain transactivating activity are thus included within the invention. The nucleic acids may be incorporated into constructs of the foregoing operatively associated with a heterologous promoter (e.g., an inducible promoter), and the constructs provided on vectors for transient transfection or stable transformation of host cells as described in greater detail below.

In some embodiments, the plant virus capsid is that of a Tombusvirideae, particularly a P-domain containing Tombusvirideae. Typically, the pores are opened at one or more (e.g., a plurality) of the three-fold axes of symmetry of the capsid (of which there are sixty in viruses such as RCNMV).

"A method of enclosing" a compound of interest in plant viral capsids as used herein refers to treatment of plant viral capsids with a chelating agent to open cavities in the plant viral capsids, permitting a compound of interest to infuse into the plant viral capsids and closing the cavities in the plant viral capsids by incubating the plant viral capsids with divalent cations.

Figure 7:
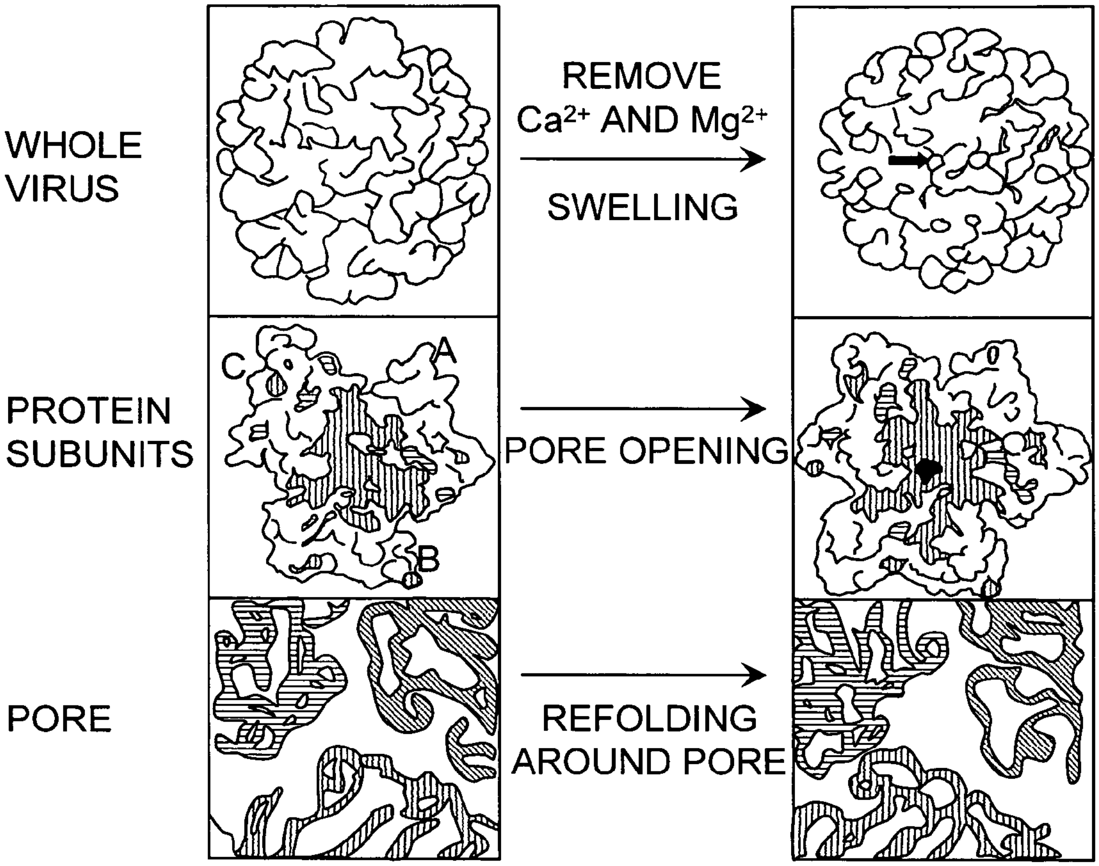
FIG. 7. Dynamic transitions of red clover necrotic mosaic virus (RCNMV). Units of three capsid protein (CP) subunits rotate to open a pore that can be used for release of drugs. (V. R. Basnayake, et al., *Virology,* 345:32-539 (2006)).

"Divalent cation switch" as used herein refers to the reversible opening in plant viral capsids of channels that extend into the interior of the capsid in an environment low in calcium and magnesium, which allow for the movement of compounds of interest into and out of the plant viral capsids. In the closed form, the virus does not contain pores (FIG. 7 shows the open and closed forms of the RCMNV viral capsid). In some embodiments divalent cations include magnesium, calcium, or a combination thereof.

"Chelating agent" as used herein refers to an organic compound capable of forming coordinate bonds with metals through two or more atoms of the organic compound to form a chelate. In some embodiments the chelating agent is ethylenediamine tetraacetic acid (EDTA). In the present invention, "sensitized viral capsids" refer to plant viral capsids that have be treated with chelating agent to remove divalent cations from the plant viral capsid, thereby opening channels therein.

In the present invention, "treating" plant viral capsids refers to co-incubation of plant viral capsids with a chelating agent or divalent cation to cause either opening or closing of channels in the plant viral capsid.

In further embodiments, the present invention provides a method of enclosing a compound of interest in plant viral capsids comprising the step of separating said plant viral capsids from excess compound of interest. In some embodiments of the invention separating refers to dialysis. In some embodiments of the invention separating refers to affinity chromatography. In some embodiments of the invention separating refers to ultracentrifugation, wherein ultracentrifugation results in pelleting of the plant viral capsids out of an aqueous solution and is followed by resuspension of the plant viral capsids in an aqueous solution that does not contain a compound of interest.

In some embodiments of the present invention, a time sufficient for said compound of interest to enter sensitized capsids includes, but is not limited to, 12-16 hr, 10-18 hr, 5-24 hr, and 1-30 hr.

Where the active compound per se is cationic rather than anionic, that active compound can be first conjugated to an anion or polyanion (e.g., a lipid, a nucleic acid) and the conjugate so formed then internalized as described above (see, e.g., U.S. Pat. Nos. 7,323,594; 7,166,745; and 7,098,032).

D. TARGETING OF CAPSIDS

In some embodiments of the present invention the method of enclosing a compound of interest in plant viral capsids further comprises the step of coupling at least one targeting compound to said plant viral capsids before or after said separating step.

"Coupling" as used herein refers to covalent attachment of targeting compounds to amino acid residues in plant viral capsid proteins. In some embodiments covalent attachment can occur at a cysteine or a lysine residue in plant viral capsid proteins.

"Targeting compound" as used herein refers to a ligand or a binding partner that specifically interacts with a proteinaceous or a non-proteinaceous extracellular structure on cells of interest. In some embodiments targeting compounds are proteins, protein fragments, peptides or non-proteinaceous chemical structures.

In some embodiments of the invention, targeting compounds can be a ligand or a binding partner that specifically interacts with an extracellular surface protein on mammalian cells of interest, said extracellular surface protein being capable of mediating endocytosis of said plant viral capsids into mammalian cells of interest.

"Extracellular surface protein" as used herein may be any extracellular surface or cell surface protein including, but not limited to, growth factor receptors, receptor tyrosine kinases, folate hydrolases, GPI-anchored cell surface antigens, pumps, and cell surface receptors including, but not limited to, G-protein coupled receptors, ion channel-linked receptors, and enzyme-linked receptors.

Extracellular surface proteins of interest may be those "differentially expressed" by a targeted cell of interest, in comparison to a cell that is not to be targeted by a plant viral capsid. For example, the cancer cells differ from normal cells in many respects, including the up- or down-regulation of numerous genes. Among the genes that are differentially regulated in cancer cells are genes that encode proteins that are expressed on the extracellular surface.

As an example, specific proteins are expressed on the extracellular surface of breast cancer cells that are not expressed (or are expressed at very low levels) by normal breast tissue cells and cells from other normal tissues. Extracellular proteins that are expressed exclusively by breast cancer cells are excellent candidates for specific targeting of malignant cells with anticancer drugs. Plant viral capsids may be internalized by malignant cells that express breast cancer cell-specific receptor proteins. The human epidermal growth factor receptor-2 (HER-2) belongs to a family of transmembrane receptors involved in signal transduction pathways that regulate cell growth and differentiation. Over expression of HER2 is associated with malignancy and a poor prognosis in breast cancer (M. Piccart, et al., *Oncology,* 61:73-82 (2001)). HER-2 is over expressed in 20% of breast cancers and is the target of therapies including the antibody treatment known commercially as Herceptin (S. H. Chiu, et al., *Journal of Controlled Release,* 97:357-369 (2004); R. Nahta, et al., *Cancer Research,* 64:2343-2346 (2004)). The over expression of EGFR (M. Ono, et al., *Clinical Cancer Research,* 12:7242-7251 (2006)), HER-2 (S. H. Chiu, et al., *Journal of Controlled Release,* 97:357-369 (2004); N. Cornez, et al., *Bulletin Du Cancer,* 87:847-858 (2000); S. Kitano, et al., *Clinical Cancer Research,* 12:7397-7405 (2006); G. Akabani, et al., *Nuclear Medicine and Biology,* 33:333-347 (2006), and CXCR4 (H. Hanaoka, et al., *Nuclear Medicine and Biology,* 33:489-494 (2006); Z. X. Liang, et al., *Cancer Research,* 65:967-971 (2005)) have led to targeted therapy using antibodies (e.g., Herceptin) and labeling using targeting peptides, including an immunoliposome approach to HER-2 targeting (Q. C. Wei, et al., *International Journal of Oncology,* 23:1159-1165 (2003); G. A. Koning, et al., *Cancer Detection and Prevention,* 26:299-307 (2002); J. W. Park, et al., *Journal of Controlled Release,* 74:95-113 (2001)). Malignant breast cancer cells can be targeted using targeting peptides that bind to HER-2.

Another example of a receptor that can be used to target breast cancer cells is CXCR4, which is known to be over expressed in hypoxic breast tumor cells (T. Slagsvold, et al., *EMBO Journal,* 25:3738-3749 (2006); P. W. Thavasu, et al., *Breast Cancer Research,* 8:S13-S13 (2006)). Like HER2, CXCR4 can be targeted with plant viral capsids coupled to CXCR4 targeting peptides. CXCR4 up-regulation is associated with hypoxia-inducible factor-1 (D. Zagzag, et al., *Laboratory Investigation,* 86:1221-1232 (2006)) and other hypoxia factors (M. Z. Ratajczak, et al., *Leukemia,* 20:1915-1924 (2006)). Antagonists to CXCR4 have been designed based on C-terminal deletion mutants of SDF-1, a natural ligand. (Y. Tan, et al., *Experimental Hematology,* 34:1553-1562 (2006)). The targeting of CXCR4 receptors using a 14 residue targeting peptide labeled with radioactive indium ($^{111}$In) (H. Hanaoka, et al., *Nuclear Medicine and Biology,* 33:489-494 (2006)). Targeted peptide therapies have been tested in vitro using the CXCR4 DV3 ligand linked to transducible anticancer peptides (E. L. Snyder, et al., *Cancer Research,* 65:10646-10650 (2005)). Additionally, malignant breast cancer cells can be effectively targeted via synergistic effects through combination of multiple targeting peptides that bind other receptors.

In some embodiments of the invention, targeting compounds can be a ligand or a binding partner that specifically interacts with an extracellular non-proteinaceous chemical structure (e.g., natural carbohydrate antigens) on mammalian cells of interest, said extracellular chemical structure being capable of mediating endocytosis of said plant viral capsids into mammalian cells of interest.

As one illustrative example, a plant viral capsid can enter a cell of interest by having a ligand or binding protein on the plant viral capsid that is specific for a cell-surface molecule or receptor and/or by using an antibody directed against a molecule on the cell surface of the plant viral capsid, resulting in complex formation between the antibody and plant viral capsid, followed by internalization of the complex.

In some embodiments plant viral capsids dock with GPCR, EGFR and chemokine class receptors leading to formation of clathrin-coated pits and endosome uptake. Without wishing to be bound to any particular theory, it is thought that this mechanism involves the formation of clusters of receptors at the cell surface that recruit the protein clathrin on the cytosolic side of the membrane forming a pit that eventually becomes a spherical endosome coated by clathrin. In some embodiments plant viral capsids dock with integrin binding domain (IBD) proteins on the cell surface, which promote the formation of lipid rafts and uptake of the plant viral capsids in caveolae.

In some embodiments targeting compounds are peptides selected from the group of peptides that specifically bind to CD46, CXCR4, EGFR, HER2, IBD, CAR, or a combination thereof (D. T. Curiel, In: Anticancer Molecules: Structure, Function, and Design, Vol. 886, pp. 158-171 (1999); S. D. Saban, et al., *Journal of Molecular Biology,* 349:526-537 (2005); S. J. Watkins, et al., *Gene Therapy,* 4:1004-1012 (1997), see Table 2). CD46 is a receptor targeted by Ad35 fiber peptide (Cusack, S., *Current Opinions in Structural Biology,* 15:237-243 (2005); D. T. Curiel, et al., *In*: Anticancer Molecules: Structure, Function and Design, Vol. 886, pp. 158-171 (1999); S. D. Saban, et al., *Journal of Molecular Biology,* 349:526-537 (2005); S. J. Watkins, et al, *Gene Therapy,* 4:1004-1012 (1997)) and Measles virus (M. K. Liszewski, et al., *Journal of Biological Chemistry,* 275: 37692-37701 (2000); M. Manchester, et al., *Virology,* 233: 174-184 (1997)). CXCR4 is a chemokine receptor over expressed in hypoxic breast cancer cells (H. Hanaoka, et al., *Nuclear Medicine and Biology,* 33:333-347 (2006)). EGFR is Epidermal Growth Factor Receptor (M. Ono and M. Kuwano, *Clinical Cancer Research,* 12:7242-7251 (2006)). HER2 is a growth factor receptor over expressed in many breast cancers (S. H. Chui, et al. *Journal of Controlled Release,* 97:357-369 (2004); R. Nahta, et al., *Cancer Research,* 64:2343-2346 (2004)). IBD is Integrin Binding Domain (A. G. Thachenko, et al., *Bioconjugate Chemistry,* 15:482-490 (2004)). CAR is Coxsackie-Adenovirus Receptor (D. T. Curiel, et al., *In: Anticancer Molecules: Structure, Function and Design, Vol.* 886, pp. 158-171 (1999); S. D. Saban, et al., *Journal of Molecular Biology,* 349:526-537 (2005); S. J. Watkins, et al, *Gene Therapy,* 4:1004-1012 (1997)).

TABLE 2

Some example targeting peptide sequences.

| Name | Amino Acid Sequence | Reference |
| --- | --- | --- |
| CD46 | CGGFSTSKRARKA (SEQ ID NO: 3) | F. Zhang, et al., *Gene Therapy*, 6: 171-181 (1999) |
| HER2 | FCGDGFYACYMDVK (SEQ ID NO: 4) | B. W. Park, et al., *Nature Biotechnology*, 18: 194-198 (2000). |
| CXCR4 | RR(NaI)CYRK(D-Lys)PYR(Cit)CR (SEQ ID NO: 5) | H. Hanaoka, et al., *Nuclear Medicine and Biology*, 33: 489-494 (2006). |
| SV40 NLS | CGGGPKKKRKVGG (SEQ ID NO: 6) | C. Feldherr, et al., *Proceedings of the National Academy of Sciences of the United States of America*, 89: 11002-11005 (1992); C. M. Feldherr and D. Akin, *Journal of Cell Biology*, 111: 1-8 (1990). |
| HIV-1 Tat protein NLS | CGGRKKRRQRRRAP (SEQ ID NO: 7) | A. G. Tkachenko, et al., Bioconjugate Chemistry, 15: 482-490 (2004). |
| Adenoviral NLS | CGGFSTSLRARKA (SEQ ID NO: 8) | A. G. Tkachenko, et al., *JACS*, 125: 4700-4701 (2003). |
| IBD-oligolysine | CKKKKKKGGRGDMFG (SEQ ID NO: 9) | A. G. Tkachenko, et al., Bioconjugate Chemistry, 15: 482-490 (2004). |

In some embodiments targeting compounds include a nuclear localization signal (NLS). See e.g., Franzen et al., US Patent Publication No. 2003/0147966. "Nuclear localization signal" as used herein refers to a polypeptide that promotes transport of the fusion protein to a cell nucleus. Amino acid sequences which, when included in a protein, function to promote transport of the protein to the nucleus are known in the art and are termed nuclear localization signals (NLS). Nuclear localization signals typically are composed of a stretch of basic amino acids. When attached to a heterologous protein (e.g., to one of the viral capsid proteins), the nuclear localization signal promotes transport of the protein to a cell nucleus. Different variations of NLS have been identified, with the SV40 large T-Antigen NLS serving as the prototype of the "classical" NLS (D. Kalderon, et al., *Cell* 39:499. (1984); R. E. Lanford, et al., *Cell* 37:801 (1984)). Other NLS that differ from the classical NLS by binding to different members of the importin α family or operating in an importin α-independent manner include the M9 sequence (H. Siomi and G. Dreyfuss, *J. Cell Biol.* 129:551 (1995)), the lymphoid enhancer factor 1 NLS (M. G. Prieve, et al., *Mol. Cell. Biol.* 18:4819 (1998)), an integrin binding domain-oligolysine peptide (A. G. Tkachenko, et al., *Bioconjugate Chemistry,* 15:482-490 (2004)) and the NLS of the HIV-1 Tat protein (A. Efthymiadis, et al., *J. Biol. Chem.* 273:1623 (1998)). In some embodiments one or more of the above listed NLS are targeting compounds coupled to plant viral capsids.

Figures 5A, 5B, 5C:
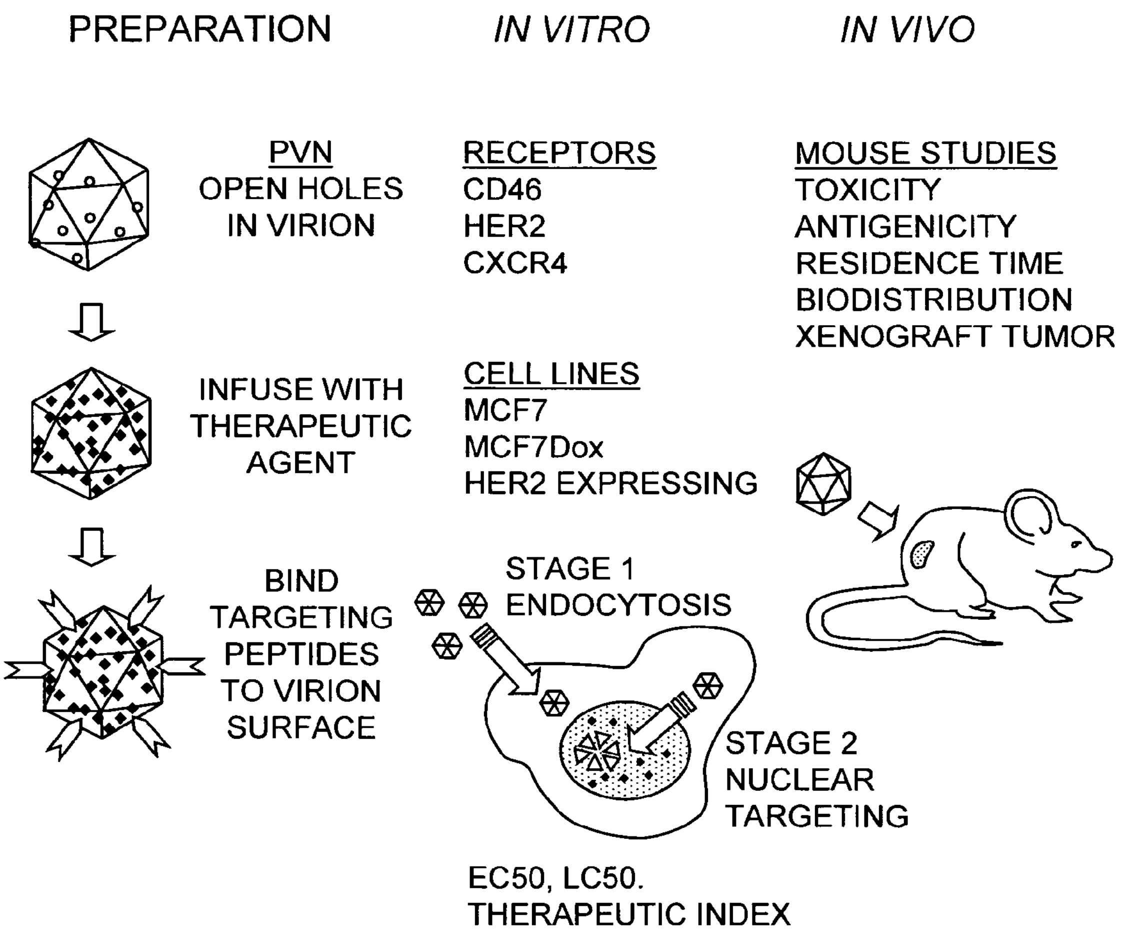
FIG. 5. Three stages using plant viral capsid cell targeting agents. (A) Preparation of loaded plant virus nanoparticles (PVNs). (B) In vitro cell targeting. (C) In vivo cell targeting.

In some embodiments nuclear targeting is desirable for anti-cancer drug delivery as these drugs act in a cell's nucleus (see FIG. 1). In mammalian cells, the nuclear pore diameter is 33-47 nm, and the pore restricts entry of molecules too large to fit. By attaching an NLS, a large object (e.g., a plant virus capsid) can be transported to the nucleus (See FIG. 5). As has been shown for Au nanoparticles, nuclear localization of PVNs is facilitated by multiple targeting signals.

Additional Sub-Cellular Targeting Peptides.

Localization in or to other organelles of the cell, including but not limited to endoplasmic reticulum, mitochondria, etc., is achieved in essentially the same manner using appropriate sub-cellular targeting peptides in like manner. The same principle discussed for nuclear localization can be used for these other types of intracellular targeting using chemical or genetic modification of the viral capsid to introduce the appropriate peptide targeting sequence for the organelle of interest. A variety of suitable sub-cellular targeting peptides are known. See, e.g., US Patent Applications Nos. 20070157328 and 20050234222; see also A. Muratovska et al., *Nucleic Acids. Res.* 29, 1852-1863 (2001); T. M-. Fu et al., *J. Virol* 72, 1469-1481 (1998).

E. FORMULATIONS AND ADMINISTRATION

In some embodiments, the present invention provides the use of a plant viral capsid of any embodiment of the present invention for the preparation of a medicament for administering said compound of interest to a subject in need thereof.

The plant viral capsids described herein can be formulated for administration in a pharmaceutically or physiologically acceptable carrier, diluent or excipient in accordance with known techniques. See, e.g., Remington, *The Science And Practice of Pharmacy* (9th Ed. 1995). In the manufacture of plant viral capsids according to the invention, the plant viral capsids are admixed with, inter alia, an acceptable carrier. The carrier must, of course, be acceptable in the sense of being compatible with any other ingredients in the formulation and must not be deleterious to the patient. The carrier can be a solid or a liquid, or both, and is preferably formulated with the compound as a unit-dose formulation, for example, a tablet, which may contain from 0.01 or 0.5% to 95% or 99% by weight of the active compound. One or more compounds of interest and/or targeting compounds can be incorporated in the formulations of the invention.

The formulations of the invention include those suitable for oral, rectal, topical (i.e., skin, hair, nails, hooves, both skin and mucosal surfaces, including airway surfaces), buccal (e.g., sub-lingual), vaginal, parenteral, transdermal, nasal, and inhalational administration, although the most suitable route in any given case will depend on the nature and severity of the condition being treated and on the nature of the particular cells of interest being targeted.

In some embodiments administration of plant viral capsids to mammalian subjects refers to parenteral injection of plant viral capsids. "Parenteral injection" as used herein refers to subcutaneous, intraveneous, intraarterial, intramuscular, transdermal, intraperitoneal or intrathecal injection.

The compounds and compositions of the present invention can be administered by any means that transports the active agents to the lung, including but not limited to nasal administration, inhalation, and insufflation. The active agents disclosed herein can be administered to the lungs of a patient by any suitable means, but are preferably administered by generating an aerosol comprised of respirable particles, the respirable particles comprised of the active agents, which particles the subject inhales. The respirable particles can be liquid or solid, and they can optionally contain other therapeutic ingredients, including, but not limited to surfactants.

Particles comprised of active agents for practicing the present invention should be administered as a formulation including particles of respirable size: that is, particles of a size sufficiently small to pass through the nose, mouth and larynx upon inhalation and into the bronchi and alveoli of the lungs. In general, respirable particles range from about 0.5 to 10 microns in diameter. Particles of non-respirable size that are included in the aerosol tend to deposit in the throat and be swallowed. Accordingly, the quantity of non-respirable particles in the aerosol is preferably minimized. For nasal administration, a particle size in the range of 10-500 μm is preferred to ensure retention in the nasal cavity. Alternatively, droplets can be given.

Liquid pharmaceutical compositions of active agents for producing an aerosol can be prepared by combining the active agents with a suitable vehicle, such as sterile pyrogen free water. Other therapeutic compounds can optionally be included.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy, which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the virus with encapsulated drug cargo and capsid-bound targeting compounds suitable for intravascular use (e.g. intravenous use) may employ a solution of physiological saline or appropriate physiological buffer in which the virus particles are suspended. Alternatively, the virus particles may be lyophilized (freeze dried) using an appropriate buffer system and subsequently reconstituted with distilled water prior to use in treating patients.

By the terms "treat," "treating" or "treatment," it is intended that the severity of the disorder or the symptoms of the disorder are reduced, or the disorder is partially or entirely eliminated, as compared to that which would occur in the absence of treatment. Treatment does not require the achievement of a complete cure of the disorder.

By the terms "preventing" or "prevention", it is intended that the inventive methods eliminate or reduce the incidence or onset of the disorder, as compared to that which would occur in the absence of the measure taken. Alternatively stated, the present methods slow, delay, control, or decrease the likelihood or probability of the disorder in the subject, as compared to that which would occur in the absence of the measure taken.

A "therapeutically effective" or "effective" amount is intended to designate a dose that causes a relief of symptoms of a disease or disorder as noted through clinical testing and evaluation, patient observation, and/or the like. "Effective amount" or "effective" can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms and body weight of the patient but also depending upon the compound being administered.

In some embodiments, the present invention provides a method of delivering a compound of interest to the nucleus of cells of interest, wherein release of the compound of interest from the plant viral capsids occurs in the nucleus of a cell of interest, which is the site of action of chemotherapeutics that target replicating cells.

In some embodiments, the present invention provides a method of delivering a compound of interest to the nucleus of cells of interest, wherein release of the compound of interest from the plant viral capsids does not occur in the cytoplasm of a cell of interest, which is the site where efflux pumps are located and can function to remove the compound of interest from the cell of interest. Without wishing to be bound to any particular theory, it is thought that the release of the compound of interest from the plant viral capsids is time-delayed by the intrinsic time constant for divalent ion transport from the virus interior to the exterior cytosol, protoplasm or solution.

F. RED CLOVER NECROTIC MOSAIC VIRUS

One example of all of the foregoing is Red clover necrotic mosaic virus (RCNMV). RCNMV is a Tombusviridae Dianthovirus. RCNMV has a number of advantages over previously used delivery platforms such as: metallic nanoparticles, liposomes, and polymeric drug delivery systems. RCNMV is a non-lipid, T=3 icosahedral soil-borne plant virus, which presents 360 lysines and 180 cysteines that can be used as labeling sites for cell targeting peptides. The RCNMV protein shell can be opened and closed based on an exquisitely sensitive divalent cation switch. The packaging of drugs (cationic or neutral) can be achieved by control of calcium and magnesium ion concentration.

The virion capsid has prominent surface protrusions and subunits with a clearly defined shell and protruding domains (M. B. Sherman, et al., *Journal of Virology,* 80(21):10395-10406 (2006)). The structures of both the individual viral capsid protein (CP) subunits and the entire virion capsid are consistent with other species in the Tombusviridae family. Within the RCNMV capsid, there is a clearly defined inner cage formed by complexes of genomic RNA and the amino termini of capsid protein subunits. An RCNMV virion has approximately 390±30 calcium ions bound to the capsid and 420±25 magnesium ions thought to be in the interior of the capsid. Without wishing to be bound to any particular theory, it is thought that depletion of both calcium and magnesium ions from RCNMV leads to significant structural changes, including (i) formation of 11- to 13-Å-diameter channels that extend through the capsid and (ii) significant reorganization within the interior of the capsid. Neither CCMV nor CPMV uses the pore opening mechanism (F. G. Albert, et al., *Journal of Virology,* 71:4296-4299 (1997)) observed in RCNMV (V. R. Basnayake, et al., *Virology,* 345:532-539 (2006)). Genomic RNA within native capsids containing both calcium and magnesium ions is extremely resistant to nucleases, but depletion of both of these cations results in nuclease sensitivity, as measured by a significant reduction in RCNMV infectivity, which indicates that divalent cations play a central role in capsid dynamics and suggest a mechanism for the release of viral RNA in low-divalent-cation environments such as those found within the cytoplasm of a cell.

Various RCNMV-based delivery applications are based on the understanding of the structure and assembly of RCNMV. The virus has a 5300 nucleotide bipartite genome (RNA-1 and RNA-2). The genome encodes 3 major proteins, a polymerase, capsid protein and movement protein. Assembly of RCNMV begins with a specific recognition of a virion RNA structure, the origin of assembly (OAS), by the capsid protein. The OAS is constituted by the formation of a kissing loop complex at a defined location in RNA-1 and RNA-2 (See FIG. 3). The binding of the capsid protein to the OAS initiates the assembly process that results in the encapsidation of the viral genome.

A RCNMV-based delivery platform has the following attributes: 1) Uniform size and shape (36 nm icosahedron); 2) Large cargo capacity (up to 1800 $nm^3$, equivalent to the volume of a 15 nm diameter nanoparticle); 3) Structurally defined chemical attachment sites (for labeling with cell surface receptor and nuclear targeting signals); 4) Ability to be produced in gram quantities (plant expression scalable); 5) Robust and stable plant viral capsid (no lipid component and stable in biological fluids); 6) Well-defined chemical infusion protocol (reversible EDTA treatment); 7) Milieu-specific intracellular drug release (cooperative kinetics of divalent ion effusion); 8) Replication restricted to plants (does not infect humans).

RCNMV has evolved the capability to be stable in soil. RCNMV is remarkably hardy and can withstand extremes of temperature and pH, organic solvents, nuclease and protease attack and ultracentrifugation. Under conditions of high calcium and magnesium, RCNMV viral capsids are extremely stable over a wide range of solution conditions. Consequently, RCNMV viral capsids are also stable in the mammalian circulatory system where the calcium ion concentration is in the millimolar range. Unlike liposomes, once inside a cell, should the calcium and magnesium concentration fall into the 100 nm range, RCNMV viral capsids structurally change into an open conformation, creating 60 11-13 Å pores extending through the viral capsids. Without wishing to be bound to any particular theory, it is thought that in nature this potentially permits the release of its genome in a newly infected cell. At higher divalent cation concentrations, as found in soil, the virus is in its closed conformation, and the genomic RNA cargo is protected. The same level of protection is conferred to any added cargo and leakage rates are very low (see Example 2). Release of encapsidated drugs is negligible in blood and other biofluids when the calcium and magnesium ion concentrations are higher than 1 mM.

The genome of RCNMV is minimal and encodes a capsid protein subunit, a movement protein and two overlapping polymerase proteins. There is no packaged replication machinery within the virion, and the four viral proteins have a low probability of adversely affecting an animal cell. Moreover, except for a small part of the genome that is required to initiate assembly of the capsid protein subunit, the genome can be altered. In some embodiments, the genome of the RCNMV itself may be altered to present RNA therapeutics to a targeted cell. Other plant viral capsids can carry significant numbers of small molecules or negatively charged polymers that replace the native genome. These molecules/polymers are not infused as described above for RCNMV, but rather reconstituted inside the virus. The reconstitution protocol requires that cargo interact with the positively charged amino acids on the interior of the plant viral capsid. This interaction creates a difference in the charge requirement of the cargo.

The capsid structures of RCNMV is described in more detail in Sherman et al., *Journal of Virology,* 80:10395-10406 (2006). The capsid structure of another Tombusvirideae virus, Cucumber necrosis virus, which has a very similar capsid structure with pores at each three-fold axis of symmetry, is described in Catpally, et al., *Journal of Molecular Biology,* 365:502-512 (2007).

Comparative Example 1

This work was addressed in the publication A. G. Thachenko, et al., *Bioconjugate Chemistry,* 15:482-490 (2004).

Design and Characterize a Library of Short Synthetic Peptides for Targeting Multi-Functional Gold Particle/Biomolecule Complexes to HeLa, NIH/3T3 and HepG2 Cells There is a significant difference in internalization efficiency between the targeting of HepG2 and HeLa cells due to the different numbers of cell surface receptors each presents. The greater number of CD46 receptors on HeLa cells explains why gold nanoparticles presenting CD46 targeting peptides are internalized readily in HeLa cells, but not in HepG2 cells. These experiments reveal significant instability of the gold nanoparticle formulation. The bovine serum albumin (BSA): nanoparticle ratio cannot be less than around 100:1 or the preparation becomes unstable. Certain peptides destabilized the BSA-coated nanoparticles. But, perhaps the most important finding was that it is difficult to load both peptides and oligonucleotides on the same nanoparticle using BSA. Direct attachment of the peptides using the thiol of a terminal cysteine was even less stable. For the experiments described below, streptavidin (SA) was used rather than BSA. The SA particles using biotin-labeled peptides and peptide nucleic acid (PNA) were sufficiently stable for cell targeting experiments with a cargo. In an attempt to find more stable and controlled formulations, encapsidation of gold nanoparticles by RCNMV was attempted as described below.

Establish Cytotoxicity of Nanoparticle Delivery Vectors

The cytotoxicity of gold nanoparticles has been determined to be peptide-dependent. Multifunctional nanoparticle formulations were tested, including the SV40 virus large T, Tat peptide, integrin binding, and known targeting peptides from the adenovirus. Extensive, as yet unpublished, data are available on the loading of cells with SV40 NLS. Cytotoxicity in HeLa cells is dependent on the peptide coverage on the nanoparticle as indicated in FIG. 1.

Figure 2A:
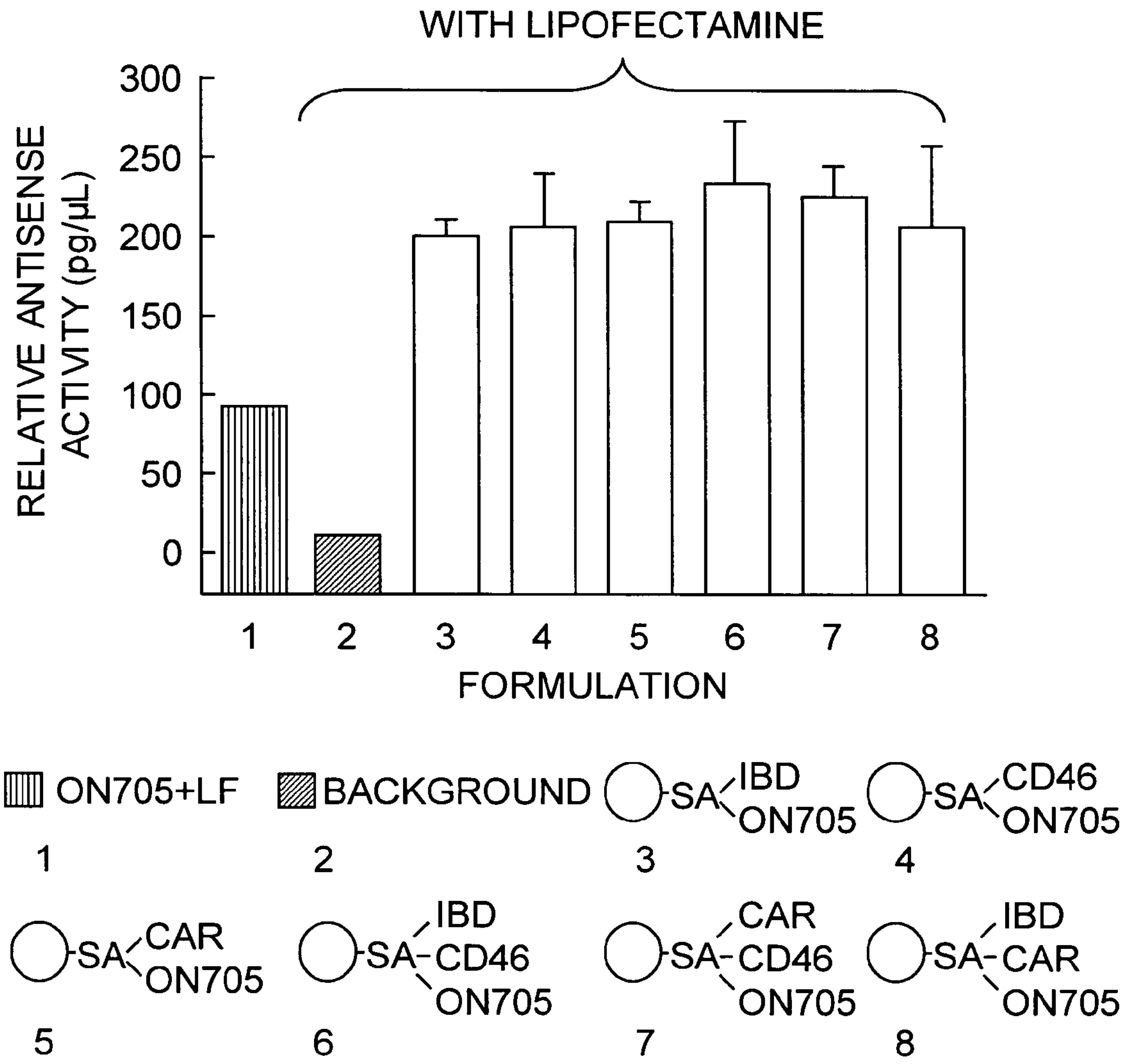
FIG. 2. Results of a luciferase gene splice assay using targeting multifunctional particles. The oligonucleotide ON705 with LF serves as a reference (red). Nuclear delivery of the oligonucleotide results in correction of splicing leading to luciferase expression. A. Comparison of multifunctional nanoparticles 3-8 with LF. The background is cells only. B. The same nanoparticles were tested without LF. The background is ON705 without LF.
Figure 2B:
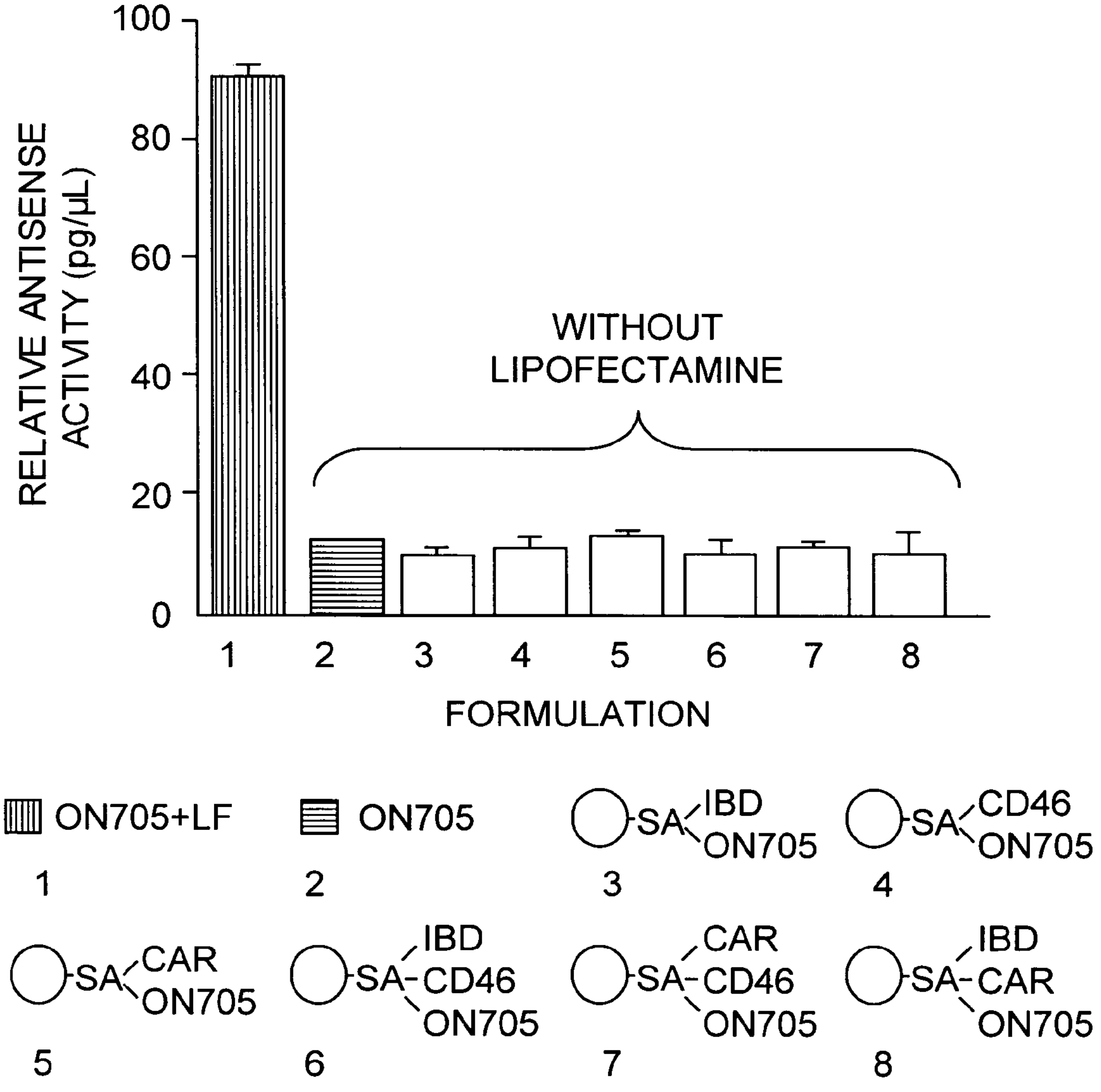

Delivery of Oligonucleotides to the Nuclei of HeLa Cells Using Nanoparticle Vectors: Study Nuclear Targeting of HeLa Cells Under Various Conditions of pH and Stress that Mimic the Environment of Tumors The antisense activity of nanoparticles containing oligonucleotides was studied in the pLuc 705 HeLa cells, in an effort to study quantitatively the potency of antisense agents for alteration of gene splicing. This cell line contains a luciferase gene with an artificial intron. The intron has a splice defect that can be corrected if the oligonucleotide ON705 reaches the splice site during transcription in the nucleus. This cell line constitutes a stringent and sensitive assay for nuclear targeting. Luciferase can be produced only if the ON705 oligonucleotide is carried into the nucleus. The control uses lipofectamine (LF), a widely-used transfection agent, for introducing genes and oligonucleotides in intracellular applications. FIG. 2A shows that gold nanoparticles (Au NPs) with targeting peptides were observed to be biologically available for hybridization in the cell nucleus with a 6-fold enhanced level of luciferase expression in the presence of LF relative to the ON705-only control. On the other hand, these formulations had no expression above background when they were introduced into the cell culture without LF. We have performed extensive characterization of the particles using gel electrophoresis, subjected the reagents to mass spectrometry and then carried out fluorescence and critical coagulation concentration (CCC) assays. We are convinced that the formulations themselves are sound and that the nanoparticles can target the cells as illustrated in FIG. 2A. However, FIG. 2B shows these same particles are not functional when taken up by endocytosis. This is one of the fundamental problems with targeted nanoparticle delivery that can be solved with the plant viral capsid platform.

Comparative Example 2

This work was addressed in the publication A. G. Thachenko, et al., *Bioconjugate Chemistry,* 15:482-490 (2004).

The Encapsidation of Nanoparticles in a PVN to Determine the Loading Capacity

Figures 3A, 3B, 3C:
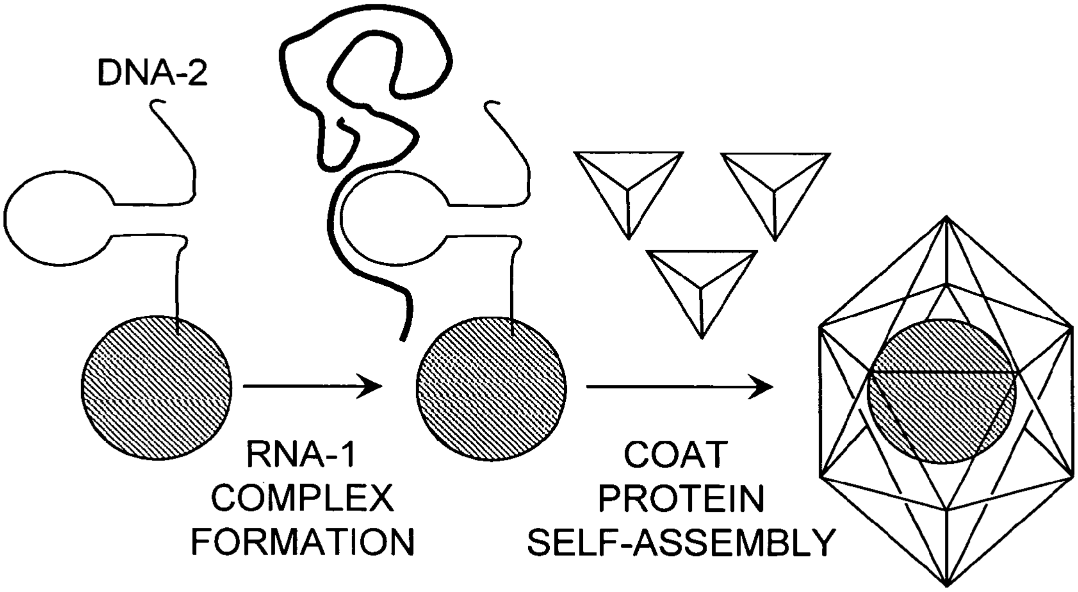
FIG. 3. Encapsidation of Au nanoparticles by RCNMV. A. Thiol-modified DNA conjugates to Au. B. RNA-1 binds to DNA to form origin of assembly (OAS). C. Coat proteins (CP) recognize OAS and polymerize around Au.
Figures 4A, 4B, 4C:
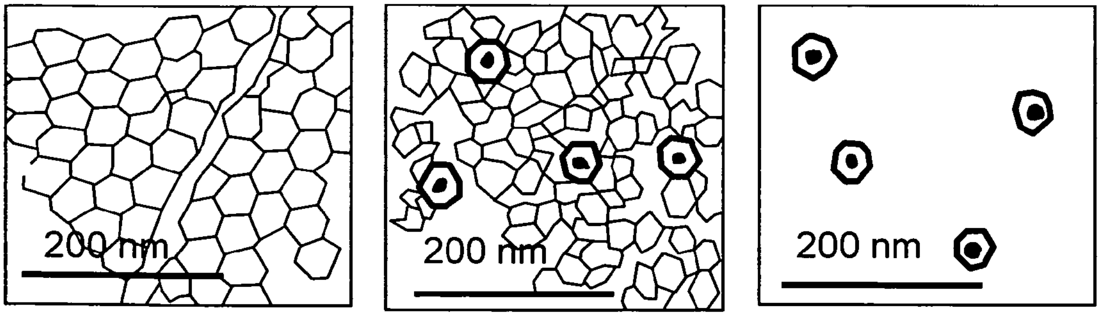
FIG. 4. TEM images of (A) native RCNMV and encapsidation of 10 nm Au nanoparticles within RCNMV protein subunits (B) prior to and (C) after purification by sucrose centrifugation.

FIG. 3A shows that an artificial RCNMV OAS can be created on a nanoparticle by the attachment of a 20 base 5'-thiol deoxyuridine modified DNA analog of the RNA-2 hairpin, known as DNA-2. This allows RNA-1 to hybridize to the stem loop forming the functional OAS (FIG. 3B), which then acts as a template for the assembly of CP to the nucleic acid complex and formation of Au-loaded PVN (FIG. 3C). The use of cognate virion RNA to trigger encapsidation of a metal nanoparticle in RCNMV demonstrates a new principle of templated self-assembly, based on previously published RNA-protein interactions (L. Loo, et al., *JACS,* 128:4502-4503 (2006)) (FIG. 4). Different size Au NPs were tested (5, 10, 15 and 20 nm). PVNs formed for 5 nm and 10 nm Au NPs, but they were smaller than native RCNMV. The 20 nm Au NP was too large to be encapsidated. Perhaps most important for the present proposal, these results demonstrate that the loading capacity of the PVN is ~1800 nm3. It is equivalent to the volume of a 15 nm diameter nanoparticle. Loading of magnetic nanoparticles and quantum dots were also demonstrated. The ability to put a nanoparticle in the PVN provides a method for understanding the fate of PVNs in cells.

Example 1

Nomenclature

Figure 8:
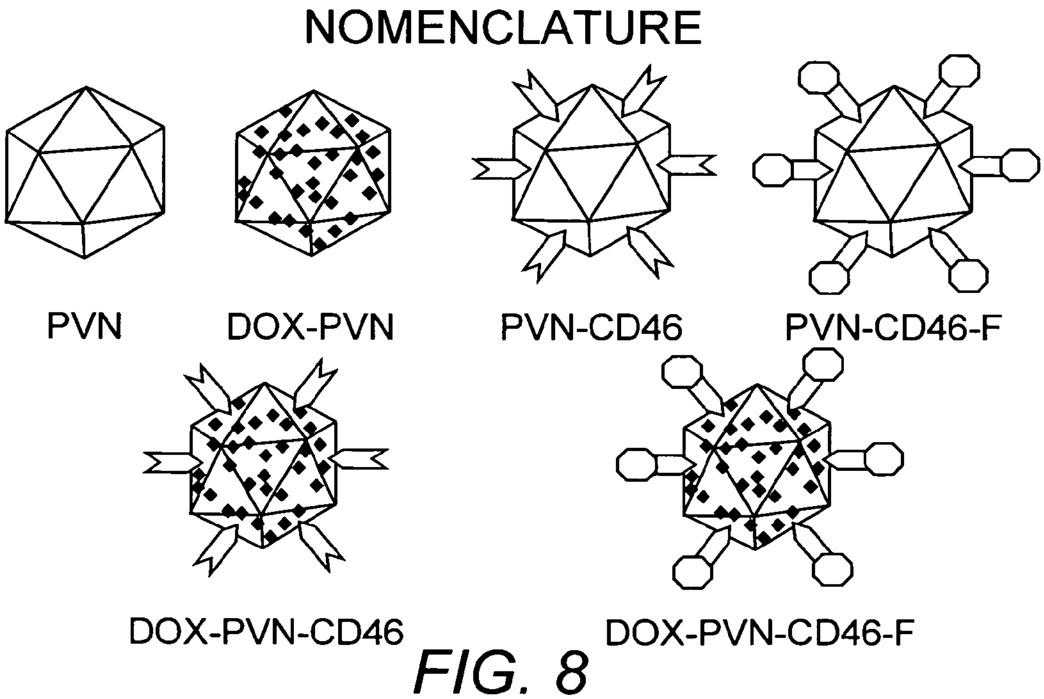
FIG. 8. Nomenclature for PVNs.

To avoid lengthy descriptions of the composition of plant viral capsids, a nomenclature for the reagents was created. The abbreviation PVN, plant virus nanoparticle, refers to RCNMV when it is used in the context of a targeted drug delivery nanoparticle. PVNs are engineered, modified, and/or infused with cargo in a variety of combinations. The abbreviations are summarized in Table 1. For example, when DOX or any small molecule is infused into the PVN, its acronym is added to the left of the PVN designation, i.e., DOX-PVN (FIG. 8). For example, if a CD46 targeting peptide is chemically attached to the exterior, its acronym is added to the right of the PVN designation, i.e., the construct is a PVN-CD46. Finally, for example, if a fluorophore such as fluorescein (F) is used as a label on the peptide the construct is designated PVN-CD46-F. Although Fluorescein is referred to, a more stable fluorophore, Alexa Fluor 633 is used. A multifunctional nanoparticle has more than one type of targeting peptide. For example, if a PVN has both a CD46 peptide and an NLS, it will be designated PVNCD46-F(NLS), i.e., the second peptide will be in parentheses.

TABLE 1

Abbreviations used in this application

| | |
|---|---|
| RCNMV | Red clover necrotic mosaic virus |
| CP | Capsid/coat protein |
| PVN | Plant virus nanoparticle |
| CXCR4 | Chemokine receptor over expressed in hypoxic breast cancer cells |
| HER2 | Growth factor receptor over expressed in many breast cancers |
| CD46 | Receptor targeted by Ad35 fiber peptide and Measles virus |
| CAR | Coxsackie-Adenoviral Receptor |
| IBD | Integrin binding domain |
| NLS | Nuclear localization signal (a peptide that interacts with importin) |
| MTT | [3-(4,5-dimethylthiazol-2-yl)-2,5-diphenyltetrazolium bromide] |
| SMCC | succinimidyl-4-(N-maleimidomethyl)cyclohexane-1-carboxylate linker |
| PEG | Polyethylene glycol |
| LF | Lipofectamine |
| Pluc | Luciferase |
| BSA | Bovine Serum Albumin |
| SA | Streptavidin |
| RME | Receptor-mediated endocytosis |

TABLE 1-continued

| Abbreviations used in this application | |
|---|---|
| RES | Reticuloendothelial system |
| FACS | Fluorescent activated cell sorting |
| MCF-7 | Estrogen/progesterone hormone receptor positive breast cancer cell line |
| MCF-7Dox | Breast cancer cell line that over expresses efflux transporters |
| MCF-7/HER2 | Breast cancer cell line that over expresses the HER2 receptor |
| MDA-MB-231 | Estrogen/progesterone hormone receptor negative breast cancer cell line |
| MDA-MB-435 | HER2 over expressing breast cancer cell line |
| DU9910 | Immortalized human breast cell line used as normal cell control |

Virus Propagation and Purification

RCNMV is propagated in 4-6 week old *Nicotiana clevelandii*. Other systemic host plants include *Nicotiana benthamiana*. Plants are maintained in a temperature controlled glasshouse at 18-26° C. Infections are initiated by rub inoculation of infectious RNA transcripts, and the infection is further propagated by sap transmission of infected tissue. Virions are harvested from plants 7-10 days post inoculation. Virions are purified as previously described with the concentration determined by UV spectroscopy with an extinction coefficient of 6.46 $cm^2$/mg at 260 nm. The virion concentration is confirmed using the Coomassie Plus Protein Assay Reagent (Pierce Chemical, Rockford, Ill.). A typical purification yields 70-100 μg of RCNMV per g of infected tissue.

The forgoing harvesting and purification of virus is intended for laboratory-scale work and can be increased by growing more plants and also by introducing larger scale purification methods, as known in the art.

Infusion of PVN with Small Molecules

To open the 60 virus pores, 5 mg/ml of highly purified RCNMV is dialyzed against 200 mM EDTA at pH 8 for 5-6 hr. Dialyzed RCNMV will be collected and incubated with dye molecules at a mole ratio of 1:2000 for rhodamine (RHO) and 1:5000 for doxorubcin (DOX) at 4° C. for 12-16 hr. To close the infused virus (PVN), after the incubation period, the sample will be dialyzed against 200 mM $Ca^{2+}$ at pH 6 for 24 hr. PVNs containing RHO-PVN and DOX-PVN, are concentrated by 10-50% sucrose gradient centrifugation (180000 g, 5° C., 55 min) in a SW-55 rotor with a model L8-70 Beckman ultracentrifuge, to remove the excess dye molecules. The sucrose gradient is then separated and collected in 15 250 μL it fractions and absorbance measurement at 260 nm. The PVN containing fractions are collected and further dialyzed and concentrated. See FIG. 6.

Attachment of Targeting Peptides to the Surface of PVNs

Figure 6:
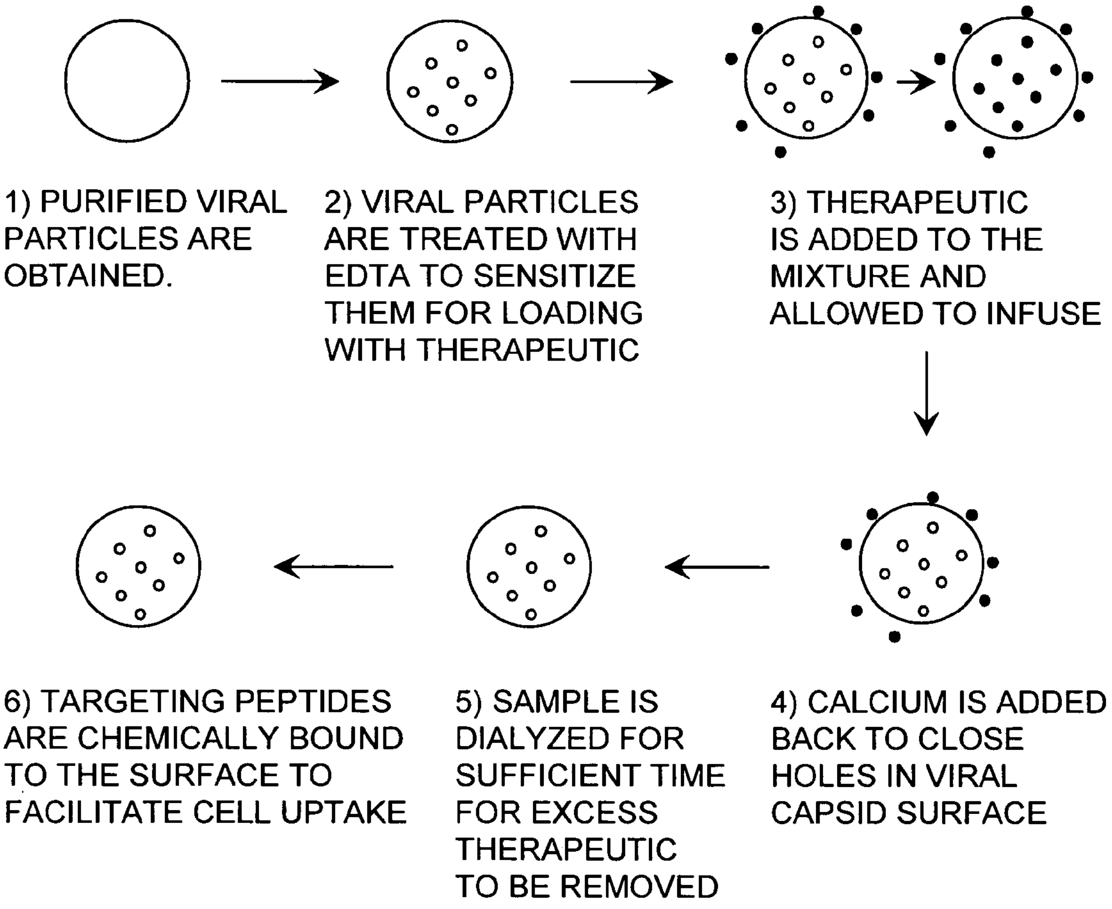
FIG. 6. Process scheme for production of plant viral capsid cell-specific therapeutic delivery device.

An effective protocol has been developed for the attachment of targeting peptides to the PVN surface lysines (see FIG. 6). See Table 2 for a list of targeting peptide sequences. Each synthetic peptide has an N-terminal cysteine added to permit attachment and to lysine residues on the PVN surface via an SMCC heterobifunctional linker. SMCC is added into PVN solution at a mole ratio of 1:1, and incubated for 30 min at room temperature. Excess SMCC is then removed by using a Microcon® centrifugal filter device with 30 kDa molecular weight cut off. Cysteine-terminated peptides (CD46 or NLS) are then added to the PVN-SMCC conjugates for 6 hr, followed by the removing of excess peptides. Alternatively, lysine-terminated peptides (CXCR4 and HER2) are added and conjugated to SMCC linkers attached to the cysteine residues on the PVN surface. The HER2 targeting peptide forms a beta-turn that is stabilized by disulfide bonds. These bonds are sufficiently stable that they are unlikely to cross-react. Binary and ternary-labeled PVNs are conjugated using mixtures of targeting peptides. For example, a binary mixture of 50% HER2 and 50% CD46 is incubated with PVN-SMCC to create a PVN-HER2(CD46) formulation.

To track the PVN during experiments a C-terminal fluorescein is attached to the peptide during synthesis. We have used fluorescein because this fluorophore is available at the UNC Chapel Hill peptide synthesis facility. Fluorescein has a high quantum yield, but has several disadvantages, such as pH sensitivity, easy photobleaching and quenching in blood. Peptides from Invitrogen with an Alexa Fluor 633 (Invitrogen) terminal label may be more suitable. Alex Fluor 633 is more stable to photobleaching, less pH-sensitive and fluoresces in a wavelength range that has less overlap with RHO and DOX.

It is important to consider alternatives to peptides that target the HER2 receptor (B. W. Park, et al., *Nature Biotechnology,* 18:194-198 (2000)). The targeting of HER-2 has also been achieved with a number of different antibodies and single-chain antibodies derived from phage display experiments (X. G. Li, et al., *Cancer Gene Therapy,* 8:555-565 (2001)). These sequences for the single-chain antibodies in a plasmid that can be expressed in *E. Coli* through a Material Transfer Agreement from Dr. Marks group at UCSF. The current form of the peptide is a 6×-histidine tagged form. To explore alternatives, one cysteine residue can be added to this sequence by site-directed mutagenesis.

Cell Cultures

Cell lines that model hormone-dependent (MCF-7), HER2 over expressing (MDA-MB-435), hormone-independent (MDA-MB-231), and P-glycoprotein over expressing (MCF-7Dox) forms of disease will be obtained from Duke Comprehensive Cancer Medical Center, Durham, N.C. Cells will be grown in controlled temperature incubators in the presence of 6-7% CO2 at pH 7.4 using DMEM media (BioWhittaker).

Cellular Delivery

For investigating the cellular localization of peptides, cells will be plated on glass coverslips and grown to 75% confluency in 6-well plates follow by incubation of PVN for various times. The coverslips will be rinsed with phosphate buffered saline and cells will be fixed with 4% paraformaldehyde in PBS for 15 min at room temperature and then rehydrated in PBS.

Quantification of Internalization by Flow Cytometry

Flow cytometry measurements were carried out with the Becton Dickinson FACSCalibur® running Cellquest Pro. Flow cytometry is sometimes referred to as “FACS” herein. The positive population of cells is determined by gating the right-hand tail of the distribution of the negative control sample for each individual cell line at 1%. This setting can then used to determine the percentage of positive cells for each of the above markers for each individual cell line.

Example 2

Molecular Infusion into Viral Capsids

Molecular infusion was tested using three dyes, RHO (positive charge), luminarosine (neutral) and fluorescein (negative charge), which were infused into opened virions (200 mM EDTA, pH 8). The PVN was exposed to a dye concentration 1000-fold higher than that of the PVN. After an incubation period, the PVNs were closed by addition of $Ca^{2+}$ and $Mg^{2+}$ combined with a titration to pH 7. Following dialysis, the fluorescence of the PVN samples was lowered to near background levels. Our data show that the dyes internalized in the virion are self-quenched. The self-quenching of dyes is well-known in the analogous experiment in liposomes where dyes are captured inside. The PVN samples were then reopened using 200 mM EDTA at pH 8, and the dyes were released. The PVN dye loaded was determined to be 90, 76 and 1 molecules, respectively, for the three dyes quantified by comparison with a fluorescence standard curve for each dye. While some of the infused dye is released by treatment with EDTA, treatment with the capsid disruption conditions of pH 10 and EDTA results in significantly greater dye release.

This experiment suggested that infusion of therapeutic agents is possible. The origin of the electrostatic dependence is likely due to the negative charge of the RNA genome as it forms a cage like lining inside the capsid (FIG. 7). Fluorescent analysis determined that more than 1000 DOX molecules are encapsidated per PVN. The significantly higher number of DOX molecules compared to RHO may arise because DOX intercalates in nucleic acids and may therefore load more efficiently within the viral genome. The amount of infused DOX released from the PVN by retreatment with EDTA at pH 7 is reduced compared to RHO. However, at pH 10, under conditions that cause virus disassembly the amount of DOX released is more than 10 times greater than measured for RHO. Dynamic light scattering and Transmission Electron Microscopy (TEM) analysis indicated that the integrity of the virion remained intact, and encapsidation of DOX did not significantly alter the structure or integrity of the RCNMV capsid. The DOX-PVN formulation was subsequently conjugated to targeting peptides as discussed in Examples 2-4.

Example 3

Internalization of PVNs Requires a Surface-Attached Targeting Peptide

We have observed that PVNs with targeting peptides attached to the surface can be internalized into mammalian cells. Native RCNMV was conjugated with fluorescein (F)-labeled targeting peptides: CAR-F, CD46-F and IBD-F. The peptides contained a terminal cysteine that was conjugated to the surface-exposed lysine residues on the RCNMV CP P-domains by means of the heterobifunctional linker molecule, succinimidyl-4-(N-maleimidomethyl)cyclohexane-1-carboxylate linker (SMCC). The formulations created are PVN-CAR-F, PVN-CD46-F and PVN-IBDF (see Example 1 and Table 1). The fluorescent labels served to monitor both the peptide coverage on the PVN surface and the uptake of PVNs by cells. Surface coverage can be determined in a fluorometer using a fluorescein standard curve to quantify the number of fluorophores in the sample and the UV-vis spectrum to quantify the concentration of RCNMV. Based on the measured fluorescence, we determined that the surface of the PVN was labeled with approximately 60 CD46-F peptides. The endocytosis of these formulations was detected using fluorescent microscopy and FACS. FACS quantifies PVN cellular uptake and cargo release in a two-channel fluorescence measurement on populations of hundreds of thousands of cells. Initially, a fixed PVN dosage at 0.15 nM concentration was used. FACS indicated that PVN intracellular uptake was targeting peptide-dependent, with PVN-CD46-F internalized in HeLa cells approximately 3-fold and 2-fold higher than PVN-CAR and PVN-IBD, respectively, after 12-hour incubation.

To eliminate the possibility that the increase in fluorescence intensity was an effect of cell auto-fluorescence, control experiments with PVN-CD46 (lacking a fluorescein label) and unmodified native PVN were assayed under the same experimental conditions. The fluorescence intensity in both cases was the same as the negative control (untreated Hela cells). Hence, the increase in fluorescence intensity from the experiment was attributed to internalization of the fluorescently labeled PVN-CD46-F. The majority of PVN-CD46-F was observed in the cytoplasm, although there was also a component inside the nucleus. Due to the efficient PVN uptake using the CD46 receptor, this peptide was chosen for subsequent studies.

A comparison study of PVN targeting HeLa and HepG2 revealed a 3-fold increase in the uptake of PVN-CD46-F in HeLa cells relative to HepG2 cells (data not shown). Although the CD46 peptide exhibited differences, the CAR peptide showed nearly the same level of internalization in HeLa and HepG2 cell lines. The control PVN-F was not internalized in either cell line. In the study, the CD46 and CAR receptors were targeted. The peptide dependent variation in internalization is similar to that which we have previously reported using gold nanoparticles. (A. G. Tkachenko, et al., *Journal of the American Chemical Society,* 125:4700-4701 (2003); A. G. Tkachenko, et al., *Bioconjugate Chemistry,* 15:482-490 (2004)). These results suggest that peptide-targeting studies are transferable from one type of nanoparticle to another.

Example 4

Internalization of RHO-PVN-CD46 Conjugates is Enhanced Compared to PVN-CD46-F

After determining that internalization required a targeting peptide be attached to the PVN, additional experiments were conducted to determine the effect infusion has on PVN internalization. A dose response curve was determined in HeLa cells at the 2-hour time point over the concentration range of 10-15 to $10^{-7}$ PVN (data not shown). When RHO-PVN-CD46-F was administered to the cells, it was found that infusion lowers the CE50 for internalization relative to PVNCD46-F. Dynamic light scattering (DLS) and TEM images indicate that PVNs are still intact after infusion.

Example 5

Internalization of RHO-PVN-CD46-F Results in RHO Release

Figure 9A:
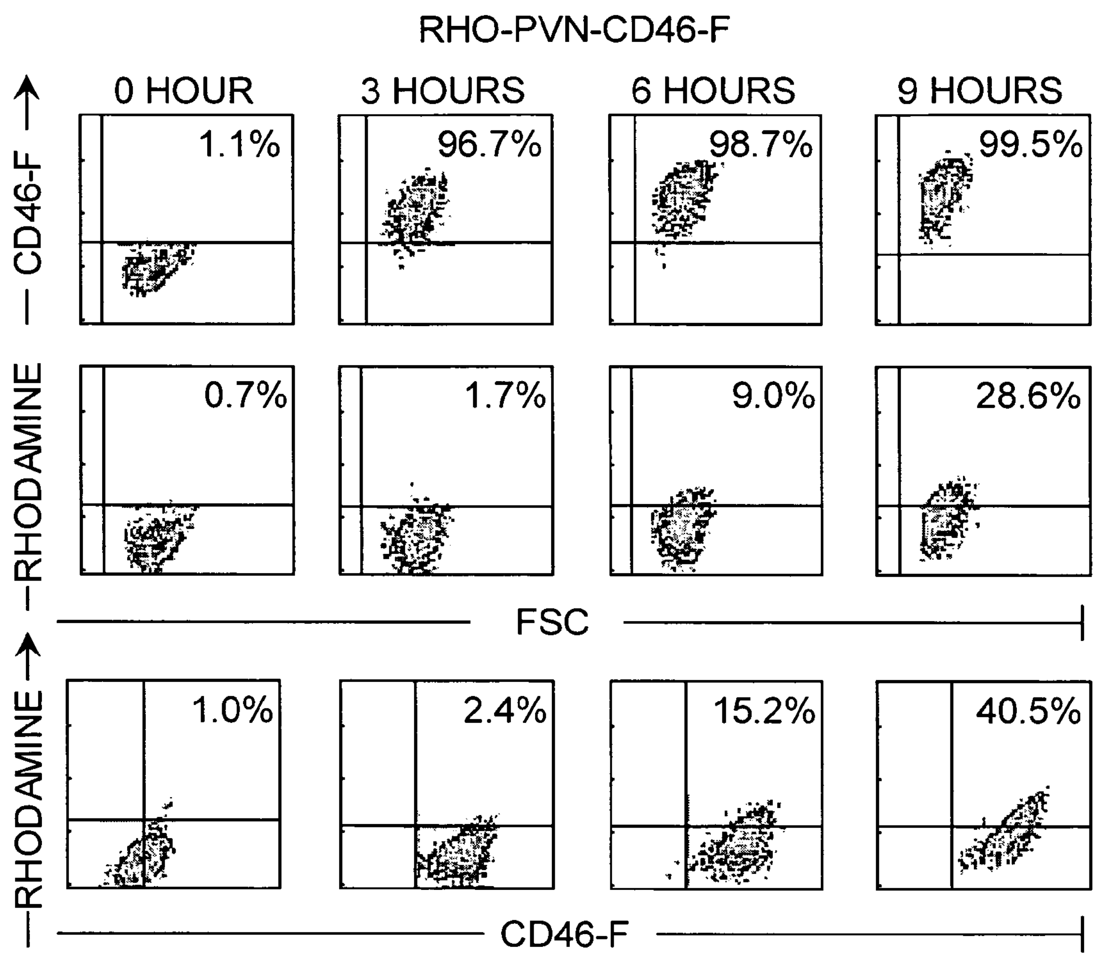
FIG. 9. FACS data for PVN with a CD46-F targeting peptide infused with (A) rhodamine (RHO) and (B) doxorubicin (DOX) shown as a function of incubation time.
Figure 9B:
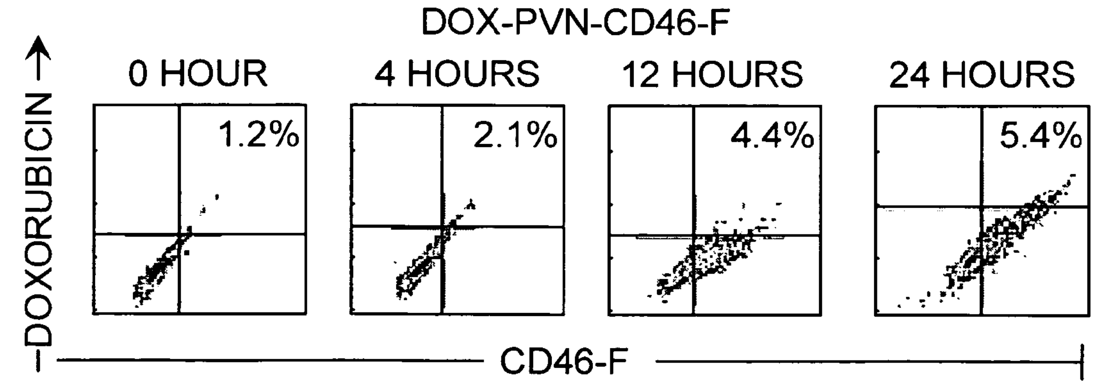

RHO-PVN-CD46-F uptake in cells was measured by FACS after 3, 6, and 9 hours. RHO-PVN-CD46-F was internalized in more than 95% of the cells after 3 hr incubation (FIG. 9A). By contrast, the fluorescence intensity of RHO in cells was not significant at the same 3-hour time point (FIG. 9A) but gradually increased to 28.6% after 9 hours of incubation. These data suggest that there is a delay of several hours between PVN internalization and RHO released. Control experiments with RHO-PVN showed no fluorescence above the negative control (untreated HeLa cells) over a 6 hour incubation period. The RHO-PVN-CD46-F experiments are important for comparison with DOX-loaded PVNs since the cytotoxicity of RHO is relatively low. FIG. 9B shows that the corresponding experiments with DOX-PVN-CD46-F result in higher levels of PVN internalization detected by FACS. However, the measured level of DOX release is low, likely due to its cytotoxic effect. Overall, the results are consistent with a significant enhancement in the uptake and cytotoxicity of DOX from DOX-PVN-CD46-F relative to free DOX.

Example 6

Doxorubicin Infused in PVNs is Therapeutically Active

Figure 10A:
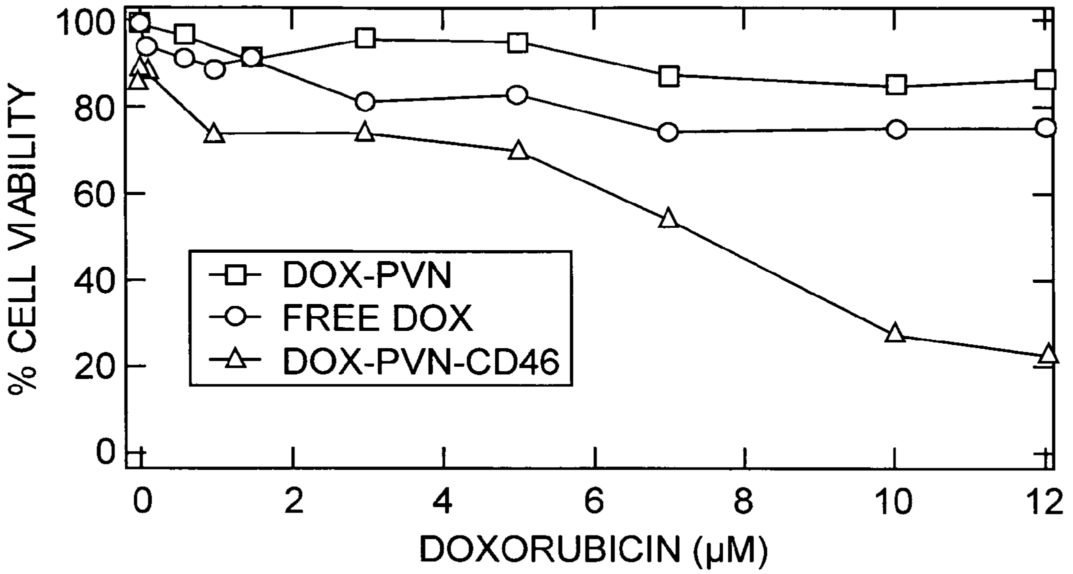
FIG. 10. Cytotoxicity of DOX determined by (A) MTT assay and (B) FACS. (A) Cytotoxicity data and relative intensity of fluorescence for Dox-PVN-CD6 in Hela cells after 24 hr exposure. (B) Cytotoxicity and internalization of PVNs and DOX delivered as free drug or infused in DOX-PVN-CD46 after 3 hr exposure in Hela cells.
Figure 10B:
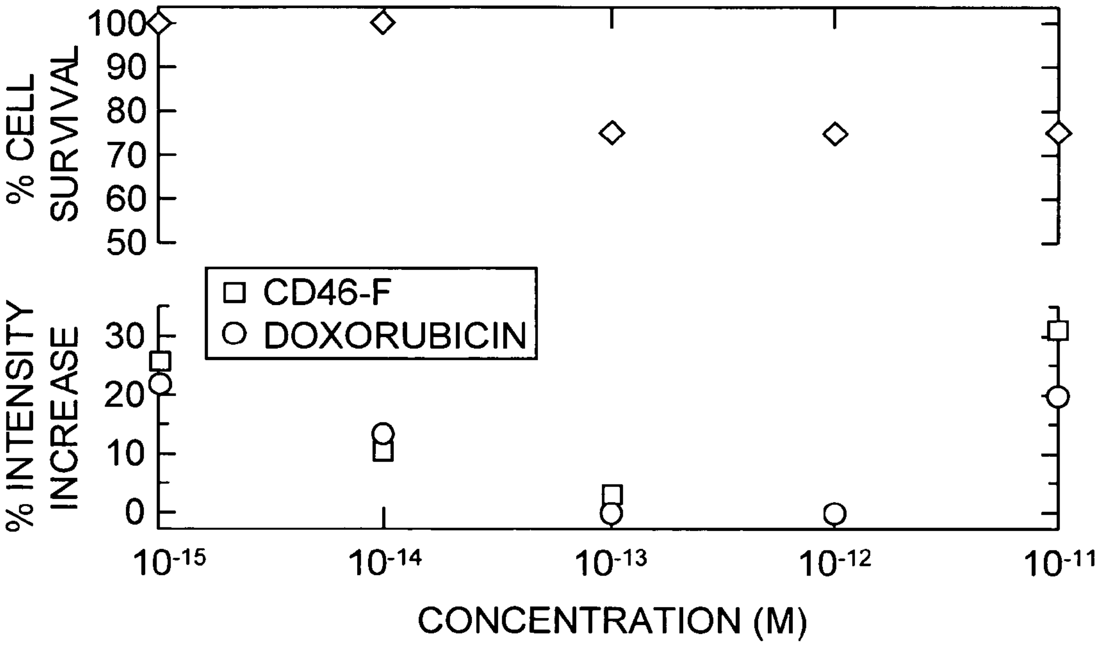

The effect of DOX-PVN-CD46 on cell viability was measured using an MTT assay (FIG. 10A). HeLa cells were exposed to a free DOX, DOX-PVN, and DOX-PVN-CD46 for 24 hours at DOX concentrations ranging from 0.01 uM to 12 uM prior assaying. Results indicated that 50% loss of cell viability was observed when a concentration of 7 uM of DOX infused in DOX-PVN-CD46 was delivered into HeLa cells ($IC_{50}$=7 uM). On the other hand, the percentage of viable cell was approximately 70-80% when the same concentration of free DOX (7 uM) was delivered to the cells. DOX infused in DOX-PVN also showed lower toxicity (90% of cells were viable) under the same delivery conditions. This result demonstrates that delivery of DOX infused in DOX-PVN-CD46 has a significant increase in cytotoxicity compared to free DOX, while DOX in DOX-PVN is sequestered and is less available than free DOX. The PVN has two desirable properties as a drug delivery platform. First, it sequesters drugs effectively in blood and other biofluids. Second, it delivers drugs inside cells triggered by divalent ion concentration and with a timed release that increases the efficacy of drugs that rely on interactions with DNA. FACS was used to determine the dose-response of DOX-PVN-CD46-F after a 2-hour exposure (FIG. 10B). Cell detachment is an early sign of apoptosis. One method to determining cell survival is to count the number of adherent cells. At a PVN concentration of 1 pM, the number of adherent cells is reduced by approximately 25% (FIG. 10B). The FACS experiments in the lower panel of FIG. 10B counts only the adherent cells. Thus, the reduction in viable (adherent) cells accounts for the low levels of PVN internalization measured by fluorescence intensity. The number of adherent cells decreases to 50% at a DOX-PVN-CD46-F concentration of 100 μM (data not shown).

Example 7

Preliminary Results on PVN Pharmacokinetics

Prior to initiating major in vivo studies, a preliminary murine study was conducted to gather basic pharmacokinetic data on the PVN. The in vivo study was designed to answer two key questions: 1) Are PVNs acutely toxic at therapeutically relevant concentrations? 2) Does the PVN formulation administered intravenously accumulate in any major organ?

Figure 11A:
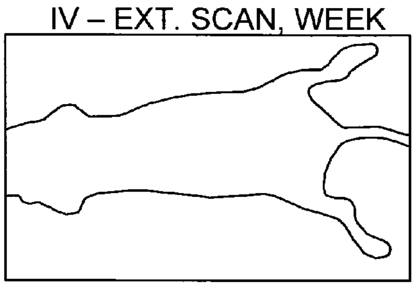
FIG. 11. Internal and External whole body fluorescence scans of nude mice.
Figure 11B:
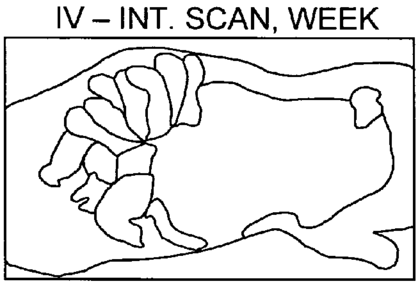
Figure 11C:
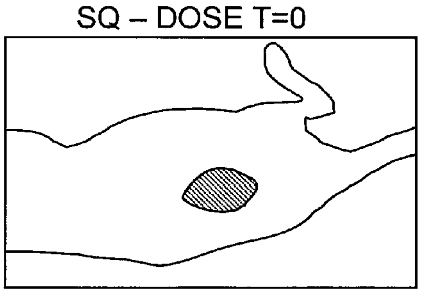
Figure 11D:
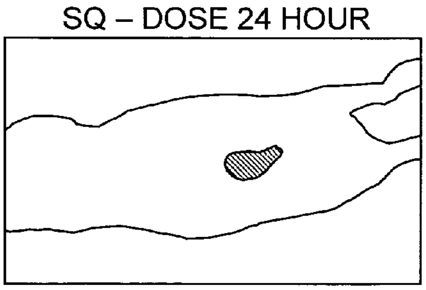

Nude mice (5 per treatment) were administered a 40 μL intravenous injection of 12 mg/mL PVN-F. As a control, the identical dose was administered subcutaneously to a sixth mouse. This corresponded to a 3 mg/kg dosage of PVN. No adverse reactions were observed in any of the mice 3-weeks post-inoculation. Based on this study, it was determined RCNMV-F is not acutely toxic when administered to nude mice. To monitor the fate of the PVN, whole body external fluorescence scans were conducted using an Olympus OV100™ whole mouse fluorescence imaging system. In the mice with intravenous delivery, whole body scans were conducted at ½, 1, 2, 3, 4, 6, 12, and 24 hour periods post delivery. No fluorescence was detected at any of these time points. In addition, one mouse per week for a total of three weeks was sacrificed and internal and external scans (FIGS. 11A & 11B) were completed to provide an indication of viral/fluorophore bioaccumulation. FIG. 11B indicates no internal accumulation of fluorescence after week 3. To verify PVN-F detectability, a subcutaneous dose was delivered to a nude mouse and monitored at 30 minute, 12 hour, 24 hour and 5 day time points. The fluorescence was easily detected at the 30-minute time point (FIG. 11C). The 12-hour time point exhibited a marked decrease in the amount of fluorescence. Fluorescence was still present 7 days post-dosing (FIG. 11D), though significantly reduced from the initial image.

Figure 12:
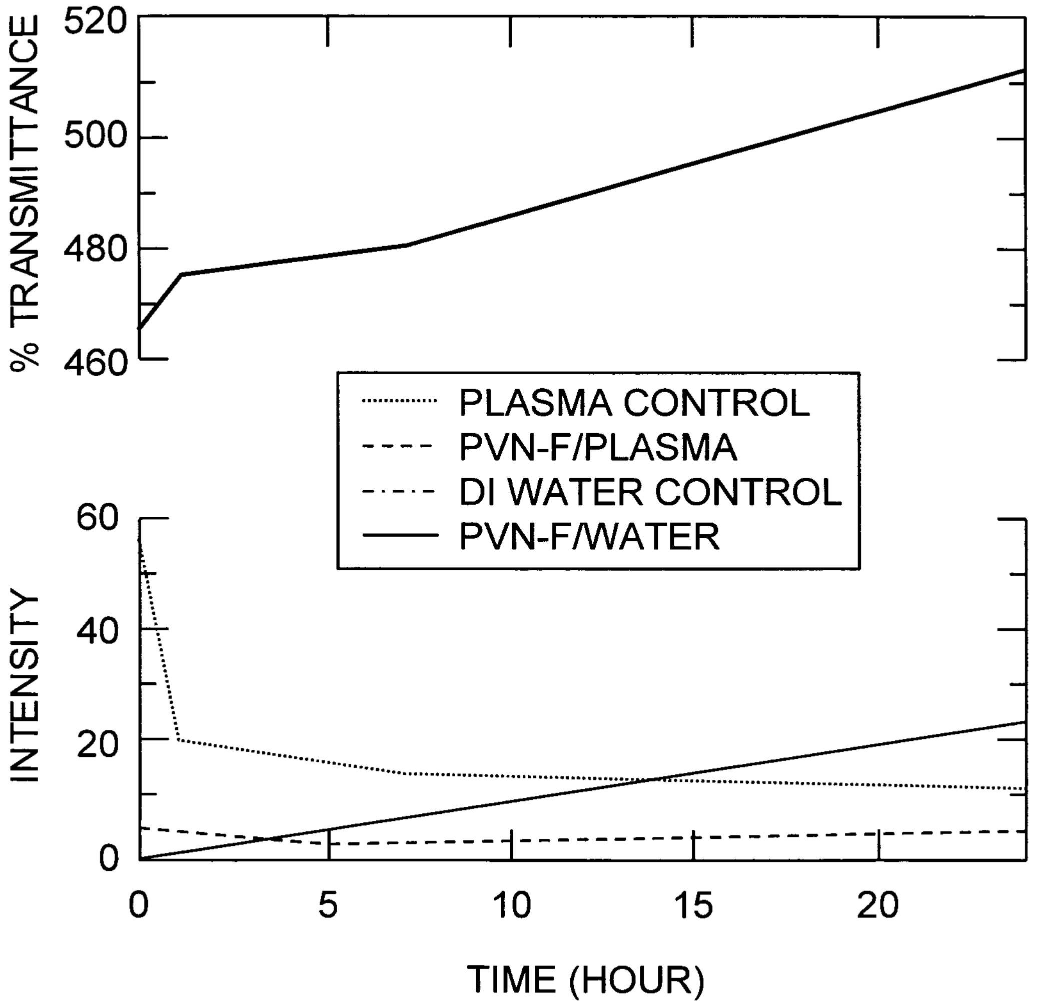
FIG. 12. Fluorescence detection of Fluorescein in mouse plasma.

To summarize, there was no internal or external fluorescence detected. Accumulation of PVNs was not observed in any tissue or organ based on whole body fluorescence. The lack of observable fluorescence in murine whole body scans even at 15 minutes post delivery is likely due to fluorescein quenching by blood proteins. When PVN-F is exposed to mouse plasma in vitro, significant quenching occurs (FIG. 12). This result was similar to that observed for polyethylene glycol (PEG)-F conjugated CPMV, where rapid quenching within 1 hour, and subsequent loss of signal within 4 hours, was observed. To test this effect, PVN-Fs were suspended separately in mouse plasma and distilled water followed by fluorescence determination using a Perkin Elmer model LS50B Luminescence Spectrometer. The concentration of each sample was formulated to simulate the in vivo study; 20 μL of 12 mg/mL PVN-F was suspended in 750 pit of sample (total blood volume for the mouse was estimated at 1.5 mL). The pH of the DI water suspension was adjusted to approximately that of the pH 7.58 PVN-F suspension. Fluorescence was measured at t=0, 1, 7, and 24 hour time points. As seen in FIG. 11, there was a significant drop in the intensity of the PVN-F fluorescence, while there was minimal change in intensity for the DI water sample. As a consequence of these studies and other general concerns regarding the stability of Fluorescein, Alexa Fluor 633 as well as Fluorescein should be used for labeled peptides. Alexa Fluor 633 is more photostable, less prone to quenching, less pH-sensitive and has less spectral overlap with RHO and DOX. Despite the difficulties in detecting fluorescence in our initial study, the lack of accumulation of PVNs in vital organs and their slow release by SQ administration justifies a full animal study.

That which is claimed is:

1. A method of enclosing a compound of interest in red clover necrotic mosaic viral capsids, comprising the steps of:

(a) treating said viral capsids to remove sufficient calcium and magnesium divalent cations to open pores therein, thereby providing sensitized viral capsids;

(b) incubating said sensitized viral capsids with said compound of interest for a time sufficient for said compound of interest to enter said sensitized viral capsids; and (c) treating said viral capsids with divalent cations for a time sufficient to close said pores and enclose said compound of interest in said plant viral capsids.

2. The method of claim 1, wherein said treating step is carried out by treating said viral capsids to remove sufficient divalent cations to open pores at three-fold axes of symmetry therein, thereby providing sensitized viral capsids; said viral capsid containing an anionic origin of assembly and a polyanion.

3. The method of claim 2 wherein the polyanion comprises RNA.

4. The method of claim 1, wherein said treating step is carried out by dialysis or by contacting a chelating agent to said viral capsids.

5. The method of claim 1, further comprising the step of:

(d) separating said viral capsids from excess compound of interest.

6. The method of claim 5 further comprising the step of:

(e) coupling at least one targeting compound to said viral capsids before or after said separating step.

7. The method of claim 6, wherein:

said treating step is carried out by contacting a chelating agent to said viral capsids to remove sufficient divalent cations to open pores at three-fold axes of symmetry therein, thereby providing sensitized viral capsids; said viral capsid containing an anionic origin of assembly and a polyanion;

said compound of interest comprises an anthracycline antibiotic; and said method further comprising the step of:

(e) coupling at least one targeting compound to said plant viral capsids before or after said separating step, said targeting compound comprising a peptide that binds to cell surface receptors CD46.

8. The method of claim 6 wherein said targeting compounds comprise a ligand or a binding partner that specifically interacts with a proteinaceous or a non-proteinaceous extracellular structure on cells of interest and/or with a proteinaceous or a non-proteinaceous intracellular structure in cells of interest.

9. The method of claim 6 wherein said targeting compounds comprise proteins, protein fragments, peptides or non-proteinaceous chemical structures.

10. The method of claim 6 wherein said targeting compounds comprise a peptide selected from the group comprising peptides that bind to cell surface receptors CD46, CXCR4, EGFR, HER2, IBD, CAR, or a combination thereof.

11. The method of claim 6 wherein said targeting compounds further comprises a nuclear localization signal (NLS).

12. The method of claim 1 wherein said targeting compounds comprise a peptide selected from the group comprising a SV40 large T-Antigen-type NLS, the adenoviral NLS, the HIV-1 Tat protein NLS, the M9 sequence, the lymphoid enhancer factor 1 NLS, an IBD-oligolysine peptide, a dual function CD46 targeting peptide/adenoviral NLS or a combination thereof.

13. The method of claim 1 wherein said compound of interest comprises a positively charged or electrically neutral compound.

14. The method of claim 1 wherein said compound of interest comprises an anthracycline antibiotic or a radionuclide.

15. The method of claim 1 wherein said compound of interest comprises a fluorescent compound or chemiluminescent compound.

16. The method of claim 1 wherein said targeting compound is included onto said viral capsid surface by modification of the viral genome to produce a coat protein with an altered sequence.

17. A red clover necrotic mosaic viral capsid containing a compound of interest produced by a process of claim 1.

18. The viral capsid of claim 17 in lyophilized form.

19. A composition comprising a red clover necrotic mosaic viral capsid of claim 17 in a physiologically or pharmaceutically acceptable carrier.

20. A method of delivering a compound of interest to cells of interest, comprising:

providing red clover necrotic mosaic viral capsids of claim 17, said viral capsids further comprising: (i) a cell targeting compound coupled thereto; and then administering said viral capsids to said cells of interest in an amount effective for said compound of interest to be delivered into said cells of interest.

21. The method of claim 20, said viral capsids further comprising: (ii) a nuclear targeting compound coupled thereto so that said compound of interest is delivered into the nucleus of said cells.

22. The method of claim 21, wherein said compound of interest is released from said viral capsids in the nucleus of said cells of interest.

23. The method of claim 20, wherein said compound of interest in not released from said viral capsids in the cytoplasm of said cells of interest.

24. The method of claim 20, wherein said administering step is carried out by oral, rectal, topical, buccal, vaginal, parenteral, transdermal, nasal, inhalational, and insufflation administration.

25. The method of claim 20, wherein said cells of interest are in a subject.

26. The method of claim 20, wherein said cells of interest are cancer cells and said compound of interest is administered in a therapeutically effective treatment amount.

27. The method of claim 26, wherein said cancer cells are multidrug resistant cancer cells.

28. The method of claim 26, wherein said cancer cells are cancer stem cells.

* * * * *

UNITED STATES PATENT AND TRADEMARK OFFICE

CERTIFICATE OF CORRECTION

PATENT NO. : 9,061,076 B2
APPLICATION NO. : 12/601736
DATED : June 23, 2015
INVENTOR(S) : Franzen et al.

It is certified that error appears in the above-identified patent and that said Letters Patent is hereby corrected as shown below:

On Title Page:
Item (75) Inventors: Please correct Inventor "LiNa Loo, Raleigh, NC (US)"
to read -- LiNa Loo, Monroe, NJ (US) --

In the Specification:
Column 2, Line 46: Please correct "produced by (z)"
to read -- produced by *(i)* --

Column 8, Line 54: Please correct "T-chloro-T-phenyl-1,"
to read -- 2'-chloro-7'-phenyl-1, --

Column 26, Line 43: Please correct "in 750 pit of"
to read -- in 750 μL of --

Signed and Sealed this
First Day of March, 2016

Michelle K. Lee
*Director of the United States Patent and Trademark Office*